(12) United States Patent
Schepartz

(10) Patent No.: US 9,644,002 B2
(45) Date of Patent: May 9, 2017

(54) ALLOSTERIC MODULATORS OF EGFR AND CONSTITUTIVELY ACTIVE MUTANTS

(71) Applicant: YALE UNIVERSITY, New Haven, CT (US)

(72) Inventor: Alanna Schepartz, Wilton, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 14/341,529

(22) Filed: Jul. 25, 2014

(65) Prior Publication Data

US 2015/0031612 A1    Jan. 29, 2015

Related U.S. Application Data

(60) Provisional application No. 61/858,400, filed on Jul. 25, 2013.

(51) Int. Cl.
| | |
|---|---|
| *C07K 7/08* | (2006.01) |
| *A61K 38/12* | (2006.01) |
| *A61K 38/10* | (2006.01) |
| *C07K 14/485* | (2006.01) |
| *C07K 7/54* | (2006.01) |
| *C07K 7/50* | (2006.01) |

(52) U.S. Cl.
CPC .................. *C07K 7/08* (2013.01); *C07K 7/50* (2013.01); *A61K 38/10* (2013.01)

(58) Field of Classification Search
None
See application file for complete search history.

(56) References Cited

U.S. PATENT DOCUMENTS

| | | | |
|---|---|---|---|
| 6,103,489 | A | 8/2000 | Arakaki et al. |
| 7,084,244 | B2 | 8/2006 | Gilon et al. |
| 7,192,713 | B1 | 3/2007 | Verdine et al. |
| 7,723,469 | B2 | 5/2010 | Walensky et al. |
| 2005/0250680 | A1 | 11/2005 | Walensky et al. |
| 2006/0008848 | A1 | 1/2006 | Verdine et al. |
| 2006/0014675 | A1 | 1/2006 | Arora et al. |
| 2007/0197772 | A1 | 8/2007 | Arora et al. |
| 2010/0234563 | A1 | 9/2010 | Arora et al. |
| 2012/0040889 | A1* | 2/2012 | Nash .................. C07K 7/06 514/3.7 |
| 2012/0190622 | A1* | 7/2012 | Nyati .................. C12N 15/1138 514/9.6 |
| 2013/0251727 | A1* | 9/2013 | Schroeder .............. C07K 14/71 424/142.1 |

FOREIGN PATENT DOCUMENTS

| | | |
|---|---|---|
| WO | WO 2009/108261 | 9/2009 |
| WO | WO 2010/148335 | 12/2010 |
| WO | WO 2012/158789 | * 11/2012 |

OTHER PUBLICATIONS

Scheck et al., 2012, Bipartite Tetracysteine Display Reveals Allosteric Control of Ligand-Specific EGFR Activation, ACS Chem Biol. 7:1367-76.
Mendelsohn, et al., 2000, The EGF receptor family as targets for cancer therapy, J. Oncogene, 19:6550.
Li, et al., 2005, Structural basis for inhibition of the epidermal growth factor receptor by cetuximab, Cancer Cell, 7:301
Lynch, et al., 2004, Activating Mutations in the Epidermal Growth Factor Receptor Underlying Responsiveness of Non-Small-Cell Lung Cancer to Gefitinib, N. Engl. J. Med., 350:2129.
Kawamoto, S.A. et al., 2012, Design of Triazole-Stapled BCL9 α-Helical Peptides to Target the β-Catenin/B-Cell CLL/lymphoma 9 (BCL9) Protein-Protein Interaction, J. Med. Chem. 55:1137-1146.
Mahon, A.B. and Arora, P.S., 2012, Design, synthesis and protein-targeting properties of thioether-linked hydrogen bond surrogate helices, Chem. Commun. 48:1416-1418.
Chapman, R.N. et al, 2004, A Highly Stable Short α-Helix Constrained by a Main-Chain Hydrogen-Bond Surrogate, J. Am. Chem. Soc. 126:12252-3.
Lewis, et al., 2008, Allosteric modulation of kinases and GPCRs: design principles and structural diversity, Curr. Opin. Chem. Biol., 12:269.
Schwartz, et al., 2007, Allosteric enhancers, allosteric agonists and ago-allosteric modulators: where do they bind and how do they act?, Trends Pharmacol. Sci., 28:366.
Jura, et al., 2009, Mechanism for Activation of the EGF Receptor Catalytic Domain by the Juxtamembrane Segment, J. Cell, 137:1293.
Endres, et al., 2013, Conformational Coupling across the Plasma Membrane in Activation of the EGF Receptor, Cell, 152:543.
Thiel, et al., 2007, Epidermal growth factor receptor juxtamembrane region regulates allosteric tyrosine kinase activation, Proc. Natl. Acad. Sci., 104:19238.
Boran, et al., 2012, A Potential Peptide Therapeutic Derived from the Juxtamembrane Domain of the Epidermal Growth Factor Receptor, PLoS ONE, 7:e49702.
Verdine, et al., 2012, All-hydrocarbon stapled peptides as Synthetic Cell-Accessible Mini-Proteins, Drug Disc. Today: Technol., 9:e41.
Schafmeister, et al., 2000, An All-Hydrocarbon Cross-Linking System for Enhancing the Helicity and Metabolic Stability of Peptides, J. Am. Chem. Soc., 122:5891.
Walensky, et al., 2014, Hydrocarbon-Stapled Peptides: Principles, Practice, and Progress, J. Med. Chem., 57 (15):6275.

* cited by examiner

*Primary Examiner* — Marianne P Allen
(74) *Attorney, Agent, or Firm* — Riverside Law LLP

(57) ABSTRACT

The present invention includes a novel class of allosteric modulators that target a protein having a juxtamembrane segment. In another embodiment, the allosteric modulator is a peptide mimetic that is capable of interacting with an α-helix or a coiled coil domain of a protein. In one embodiment, the peptide mimetic binds to at least an α-helix or a coiled coil domain of EGFR and modulates its activity.

3 Claims, 22 Drawing Sheets

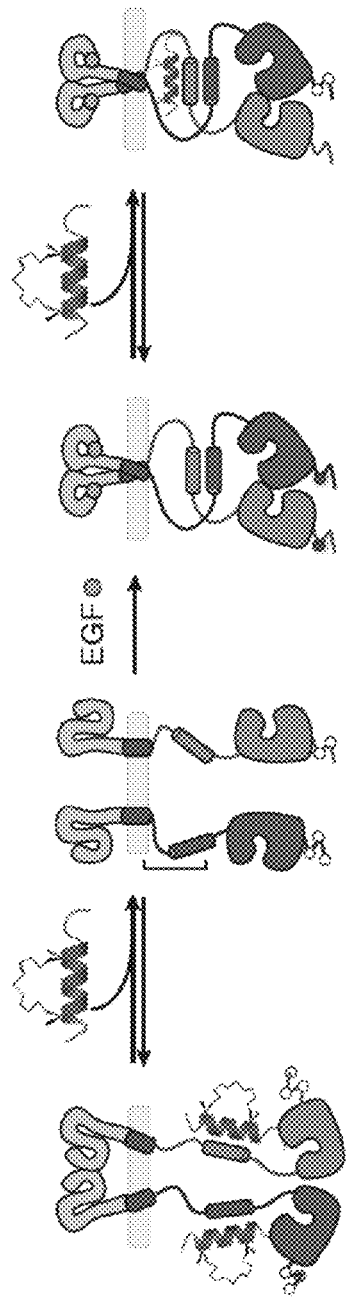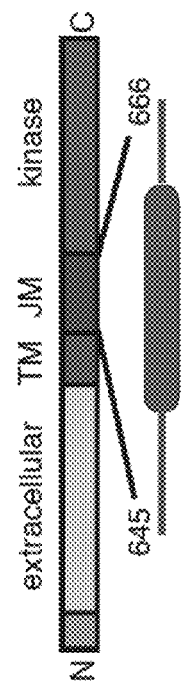
Figure 2

| name | sequence | binds EGF coiled coil | binds TGF coiled coil |
|---|---|---|---|
| WT | VRKRTLRRLLQERELVE (SEQ ID NO: 1) | Yes | Yes |
| E1 | VRKRZLRRLLQXRELVE (SEQ ID NO: 3) | Yes | Yes |
| E2 | VRKRTLRXLLQXRELVE (SEQ ID NO: 5) | Yes | No |
| E3 | VRKRTLXRLLXERELVE (SEQ ID NO: 7) | Yes | No |
| E4 | VRKRTLRBLLXERELVE (SEQ ID NO: 9 | Yes | No |
| T1 | VRKRTXRRLXQERELVE (SEQ ID NO: 11) | No | Yes |
| T2 | VRKRTLRRLXQERXLVE (SEQ ID NO: 13) | No | Yes |
| T3 | VRKRTBRRXLQERELVE (SEQ ID NO: 15) | No | Yes |
| T4 | VRKRXLRRXLQERELVE (SEQ ID NO: 17) | No | Yes |
| TE-64562 | RKKRRQRRRGRRRHI VRKRTLRRLLQERELVE (SEQ ID NO: 20) | Yes | Yes |

E1 and E2 kill cells that express EGFR: stapled and unstapled equally potent

| name | A431 [hi wt EGFR, skin] | H2030 [wt EGFR, lung cancer] | H1975 [dm EGFR, lung cancer] | H3255 [L858R EGFR, lung cancer] | IMR90 [wt EGFR, normal lung] | | SK-N-MC [no EGFR] | |
|---|---|---|---|---|---|---|---|---|
| WT | > 100 | > 50 | > 50 | > 50 | | | | |
| E1 | 2.99 ± 0.30 | 1.67 ± 0.45 | 2.24 ± 0.44 | 0.94 ± 0.34 | 1.48 ± 0.21 | 2.17 ± 1.44 | ~10 | ~10 |
| | 2.80 ± 0.41 | 1.58 ± 0.43 | 2.31 ± 0.51 | 1.91 ± 0.38 | | | | |
| E2 | 13.00 ± 2.88 | 2.39 ± 0.89 | 4.07 ± 0.37 | 2.05 ± 0.67 | 5.63 ± 0.89 | 5.31 ± 0.24 | >10 | >10 |
| | 10.00 ± 0.54 | 2.44 ± 0.88 | 4.68 ± 1.31 | 2.54 ± 0.69 | | | | |
| E3 | | ~100 | >100 | | >100 | >100 | >10 | >10 |
| E4 | | >100 | >100 | | >10 | >10 | >10 | >10 |
| T1 | >50 | >100 | >10 | >50 | >10 | >10 | >10 | >10 |
| T2 | >50 | >100 | >10 | >50 | >10 | >10 | >10 | >10 |
| T3 | | ~70 | ~50 | | ~100 | ~80 | >10 | ~80 |
| T4 | | 37.13 ± 6.16 | 11.31 ± 3.18 | 32.31 ± 9.37 | | | >100 | >100 |

Figure 5

Strategy should be applicable to other ErbB family members and other RTKs

| | | |
|---|---|---|
| EGFR | ...RRRHIVRKRTLRRLLQERELVEPLTPSG... | (SEQ ID NO: 21) |
| ErbB2 | ...RRQQKIRKYTMRRLLQETELVEPLTPSG... | (SEQ ID NO: 22) |
| ErbB3 | ...RGRRIQNKRAMRRYLERGESIEPLDPSE... | (SEQ ID NO: 23) |
| ErbB4 | ...RRKSIKKKRALRRFL-ETELVEPLTPSG... | (SEQ ID NO: 24) |
| Jak1 | ...FRAIMRDIN... | (SEQ ID NO: 25) |
| Jak2 | ...FRAIIRDLN... | (SEQ ID NO: 26) |
| Jak3 | ...FRAVIRDLN... | (SEQ ID NO: 27) |

Figure 7

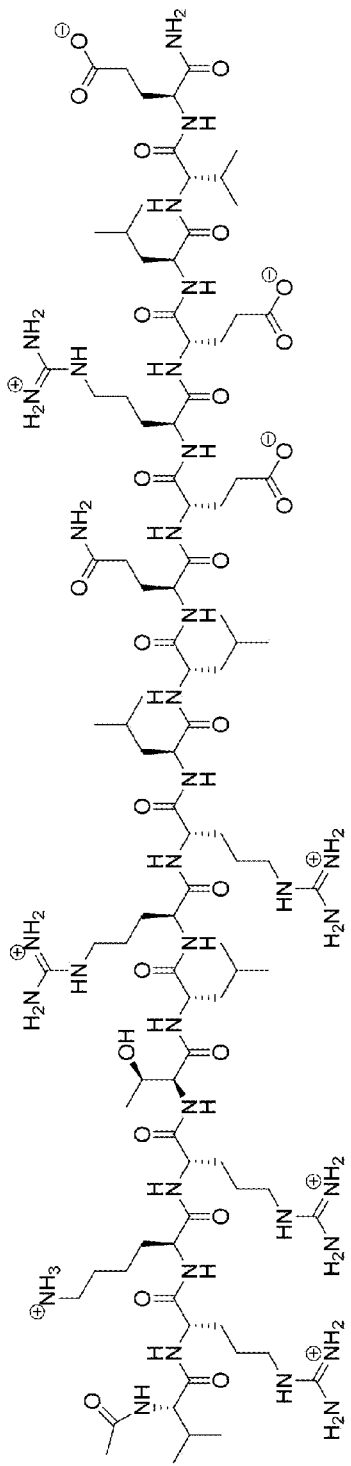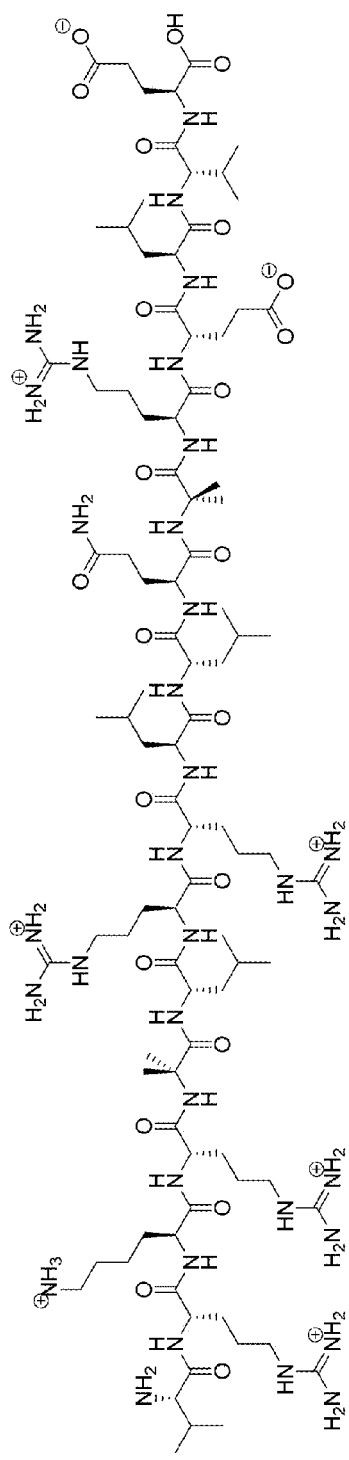
Figure 8

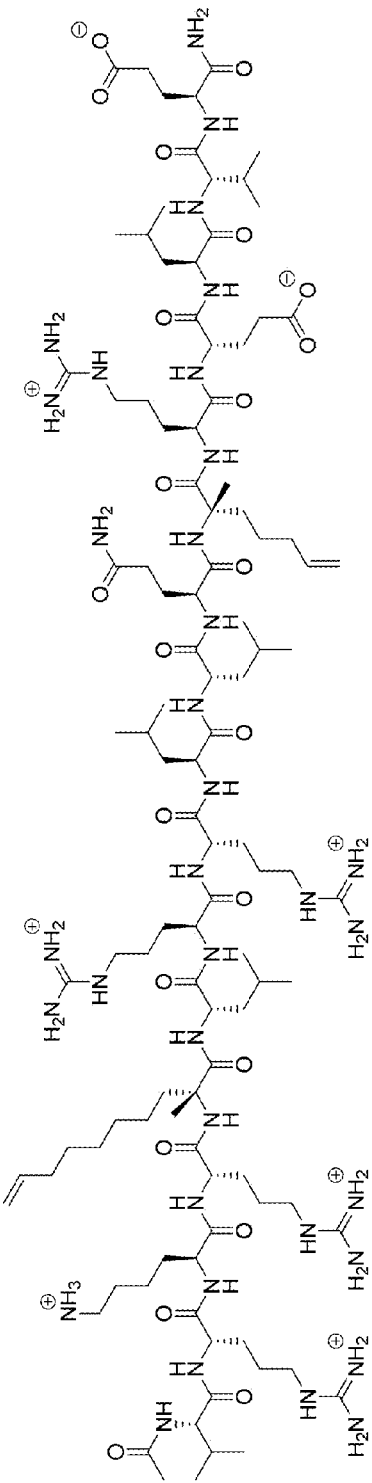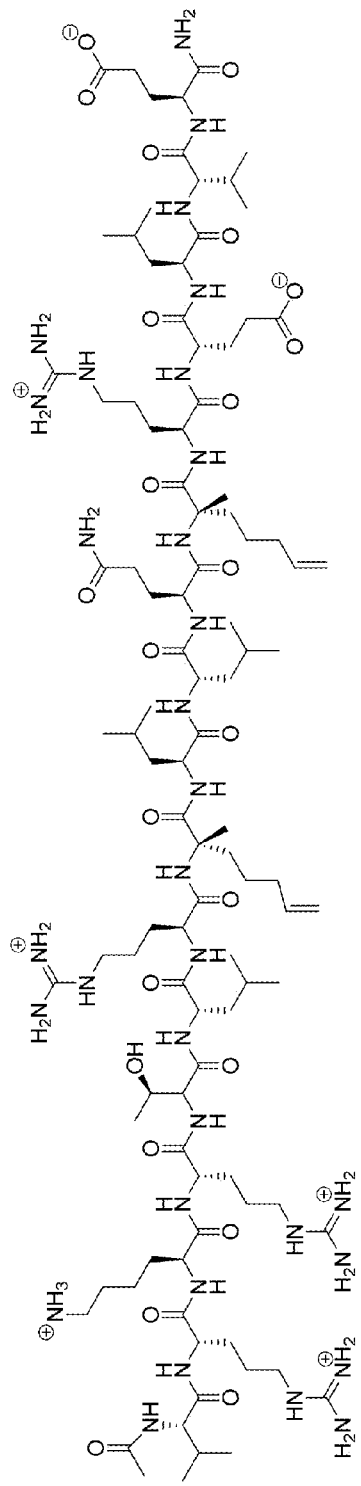
Figure 9

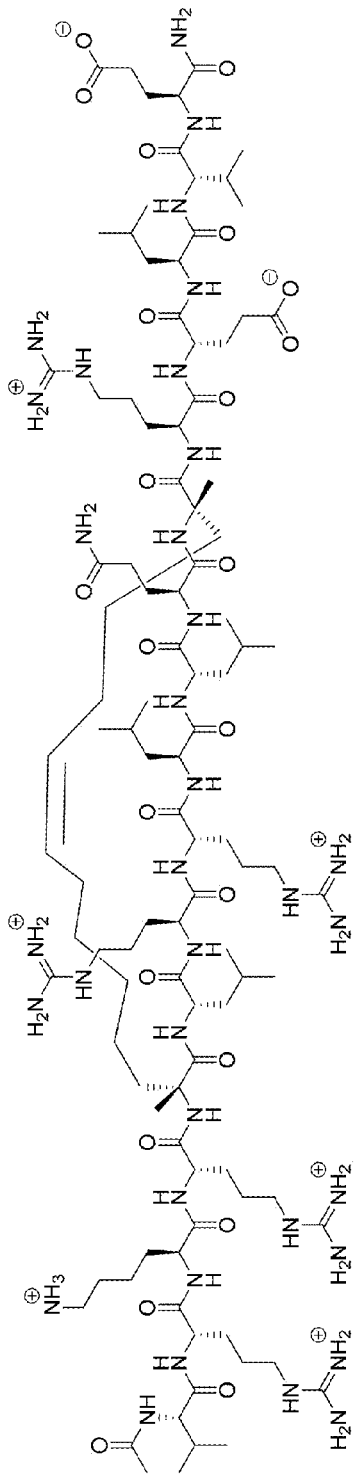
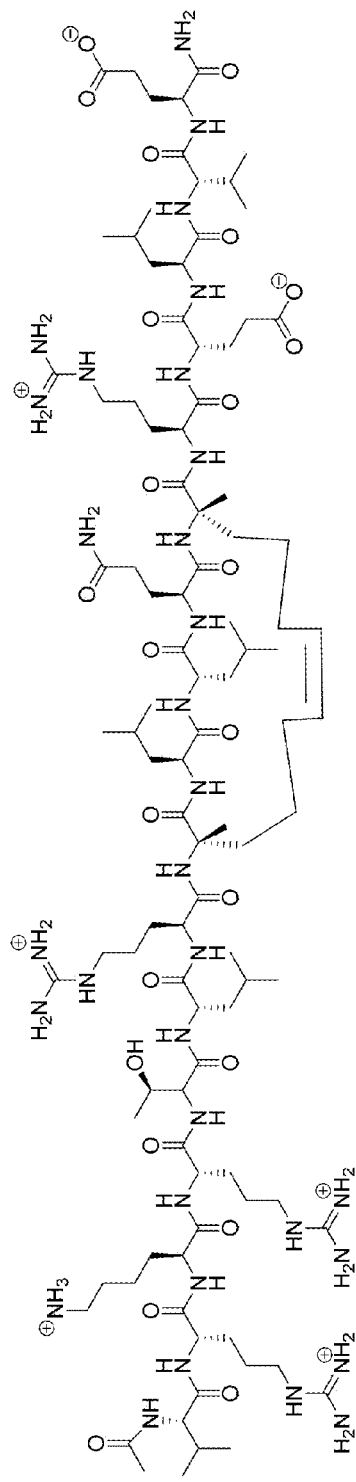
E1$^S$: Ac-VRKRR$_8$LRRLLQS$_5$RELVE-Am (SEQ ID NO: 3)
E2$^S$: Ac-VRKRTLRS$_5$LLQS$_5$RELVE-Am (SEQ ID NO: 5)
Figure 10

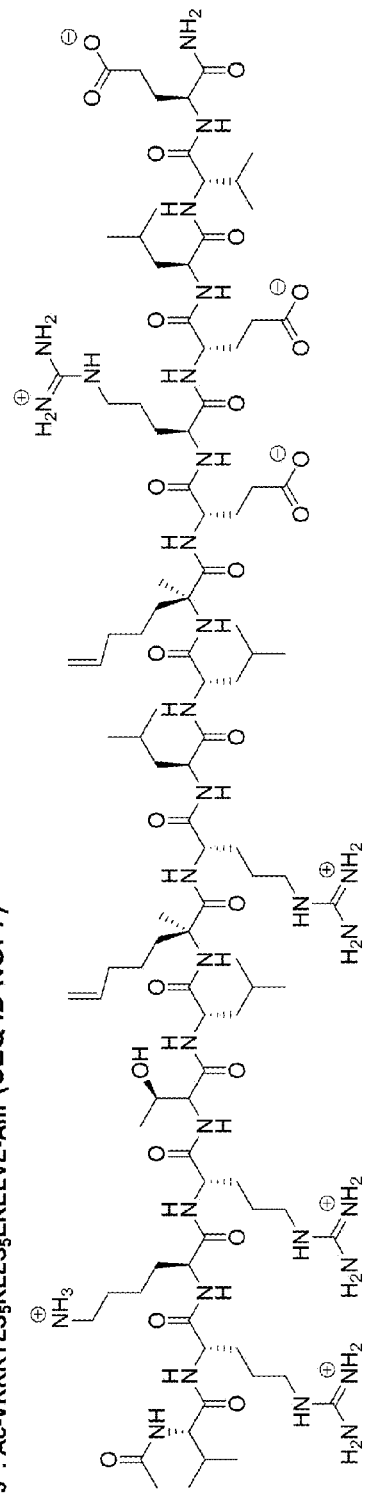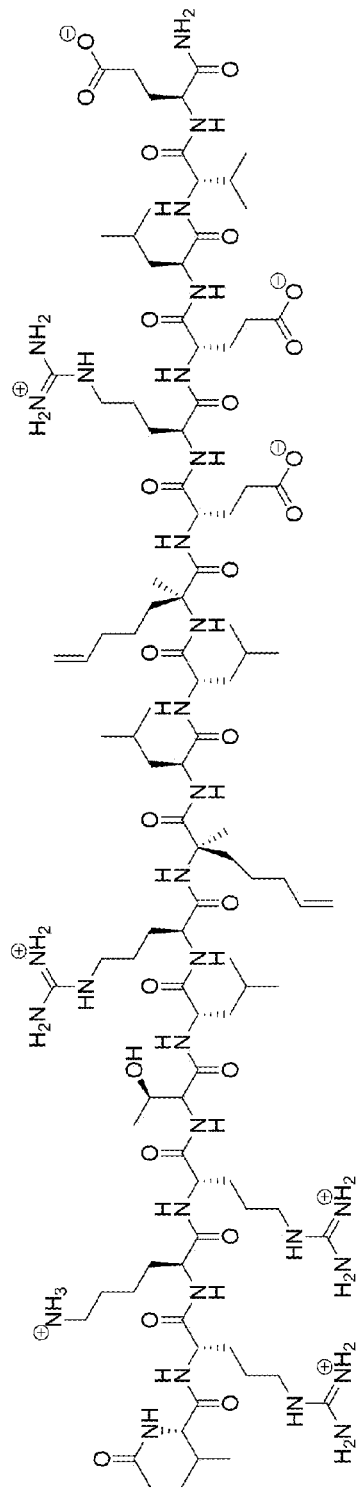
Figure 11

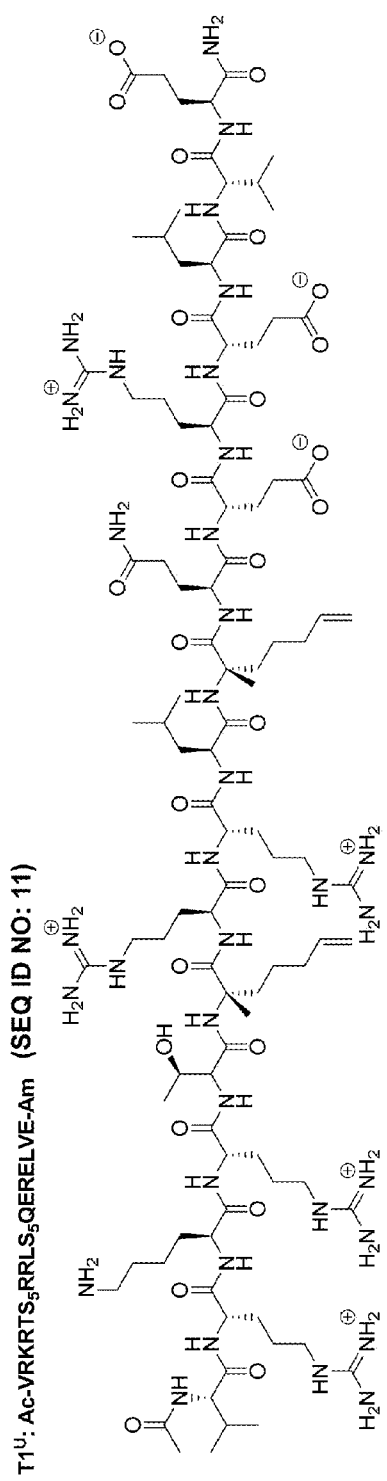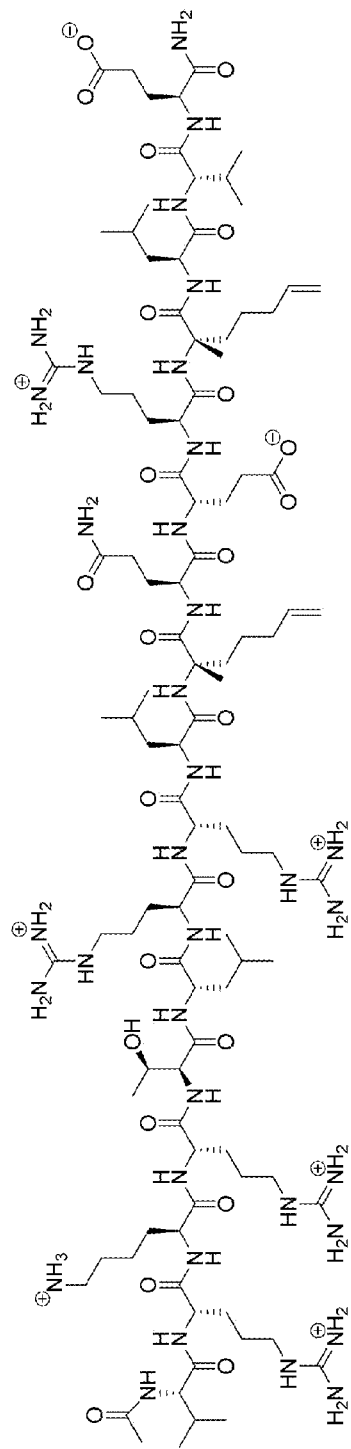
Figure 13

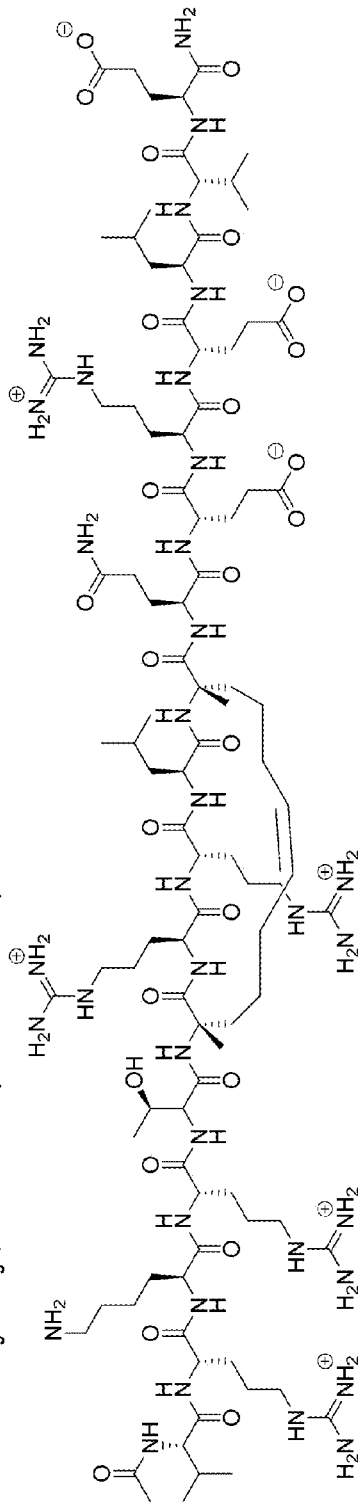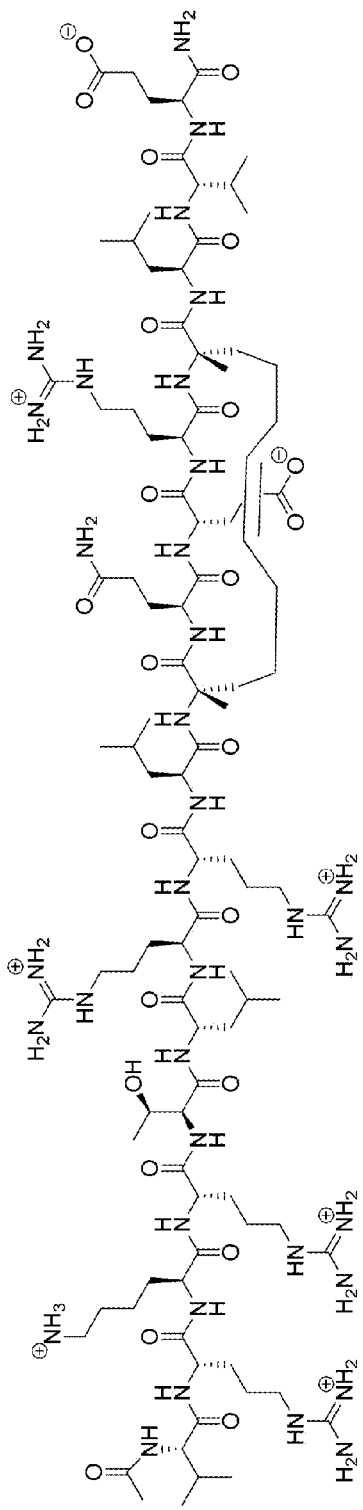
T1S: Ac-VRKRTS5RRLS5QERELVE-Am (SEQ ID NO: 11)
T2S: Ac-VRKRTLRRLS5QERS5LVE-Am (SEQ ID NO: 13)
Figure 14

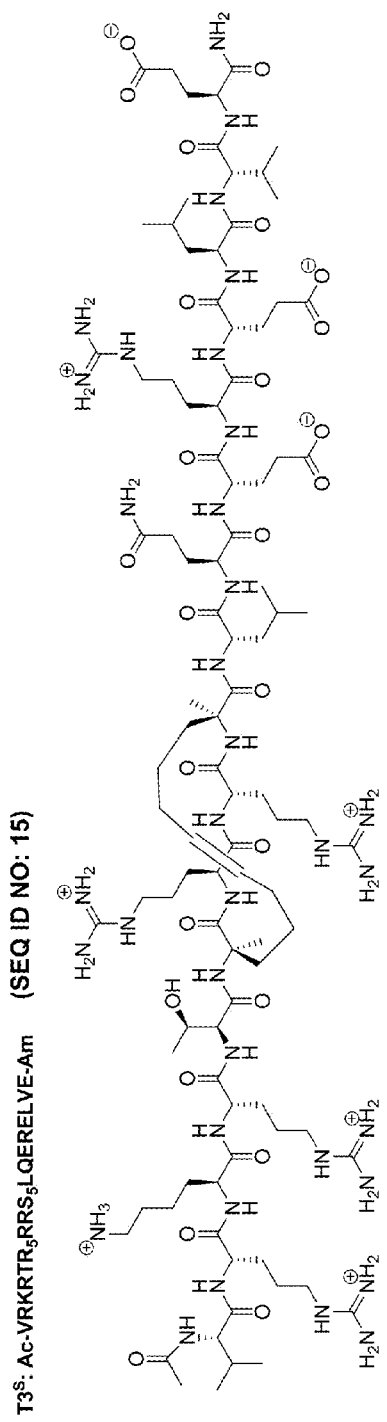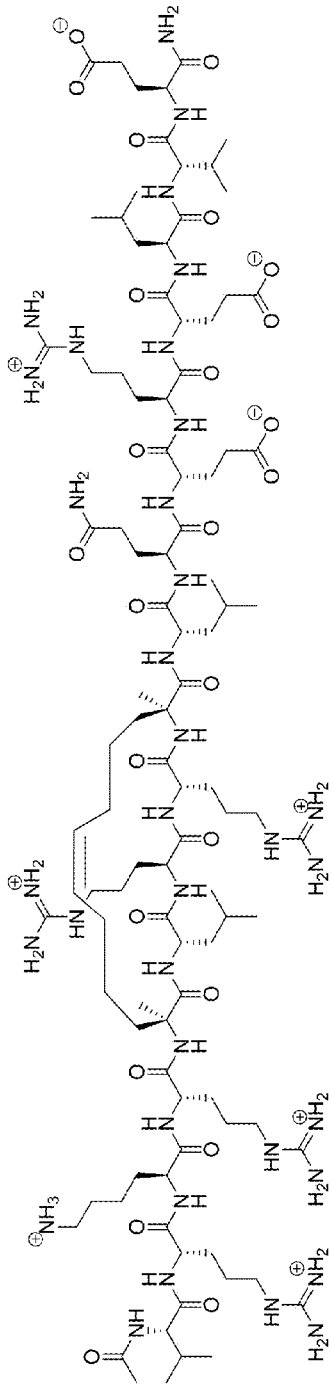
Figure 16

US 9,644,002 B2

ALLOSTERIC MODULATORS OF EGFR AND CONSTITUTIVELY ACTIVE MUTANTS

CROSS-REFERENCE TO RELATED APPLICATIONS

This application claims priority to U.S. Provisional Patent Application No. 61/858,400 filed Jul. 25, 2013, the contents of which are incorporated by reference herein in their entirety.

STATEMENT REGARDING FEDERALLY SPONSORED RESEARCH OR DEVELOPMENT

This invention was made with government support under grant number GM083257 awarded by the National Institutes of Health. The government has certain rights in the invention.

BACKGROUND OF THE INVENTION

Members of the epidermal growth factor receptor family (ErbB1/HER1, ErbB2/HER2, ErbB3/HER3, and ErbB4/HER4) are transmembrane tyrosine kinases that are activated by ligand-induced dimerization. (Schreiber et al., 1983 Journal of Biological Chemistry 258(2): 846-53; Ushiro and Cohen, 1980 Journal of Biological Chemistry 255(18): 8363-5). These receptors regulate cell proliferation, differentiation, and migration, and their abnormal activation is associated with a variety of human cancers. (Yarden and Sliwkowski, 2001 Nature Reviews Molecular Cellular Biology 2(2):127-37). Several cancer drugs (for example, Erlotinib) interact with the ATP-binding site of the EGFR kinase to halt tumor growth and increase apoptosis in cancer cells.

It is known that the EGFR kinase domain is activated after ligand-induced dimerization of the extracellular region of the receptor, although the underlying mechanism has remained elusive. Studies have shown that mutations in the catalytic domain of EGFR can either increase or decrease with the kinase activity of these proteins. (Chan et al., 1996 Journal of Biological Chemistry 27(37): 22619-23).

The epidermal growth factor receptor (EGFR/ErbB1/HER1) receives a stimulus in the form of an extracellular binding event and communicates this information across the cell membrane to effect diverse signaling outcomes (Lemmon et al., 2010 Cell 141: 1117-1134). When this communication is misregulated via overexpression or mutation, the signaling consequences are associated with a variety of human diseases, including cancer. Therefore, deciphering how EGFR conveys information across the cell membrane is essential to the understanding of its role not only in normal biology, but also in disease progression and therapeutic response (Lemmon et al., 2010 Cell 141: 1117-1134; Avraham et al., 2011 Nature Reviews Molecular Cell Biology 12: 104-117).

Activation of EGFR triggers multiple cascades of signal transduction pathways. EGFR contains at least six autophosphorylation sites that serve as docking nodes for a multitude of intracellular signaling molecules including adapter proteins and other enzymes. Therefore, rather than regulating a single linear pathway, activation of EGFR modulates entire networks of cellular signal transduction cascades. These signals affect both cell cycle progression/proliferation and apoptosis. Two signal transduction cascades that lie downstream of EGFR are the MAPK (mitogen activated protein kinase) and Akt pathways. In the MAPK pathway, EGFR activates the small GTP binding protein Ras to transfer cell growth signals through the Raf-MEK-ERK cascade, culminating in the regulation of transcription factors important for cell cycle progression.

It has been shown that the intracellular juxtamembrane segment plays a crucial role not only in receptor activation, but also in relaying the identity of the bound ligand to the cytosol (Scheck et al., 2012 ACS Chem. Biol. 7: 1367-76). Bipartite tetracysteine display was used to demonstrate that ligand binding to the EGFR extracellular domains is transmitted across the membrane into a defined dimeric helical interface within the juxtamembrane. Additionally, it was discovered that ligand identity is communicated to the cell interior through distinct juxtamembrane conformations. It was also discovered that the juxtamembrane segment plays a crucial role not only in receptor activation, but also in decoding and relaying extracellular signals to the cytosol.

Four EGFR inhibitors have been approved for use: Cetuximab (Mendelsohn, et al., 2000, J. Oncogene, 19, 6550; Prewett, et al., 1996, J. Immunother., 19, 419) is a monoclonal antibody that directly inhibits the binding of growth factors to the EGFR extracellular domain (Li, et al., 2005, Cancer Cell, 7, 301), whereas gefitinib, erlotinib, and afatinib (Ciardiello, F. 2000, Drugs, 60, 25; Lynch, et al., 2004, N. Engl. J. Med., 350, 2129; Plummer, et al., 2006, J. EJC Suppl., 4, 1731; Shepherd, et al., 2005, N. Engl. J. Med., 353, 123) are tyrosine kinase inhibitors (TKIs) that directly inhibit the binding of ATP to the intracellular catalytic domain (Yarden, et al., 2012, Nat. Rev. Cancer, 12, 553; Zhang, et al., 2009, N. S, Nat. Rev. Cancer, 9, 28). Other molecules in these two categories, including reversible and irreversible TKIs that inhibit the drug-resistant EGFR double mutant, are in clinical development (Solca, et al., 2012, J. Pharm. Exp. Ther., 343, 342; Li, et al., 2008, Oncogene, 27, 4702; Ohashi, et al., 2013, Cancer Res., 73, 2101A; Walter, et al., 2013, Cancer Discovery, 3, 1404; Ward, et al., 2013, J. Med. Chem., 56, 7025; Zhou, et al., 2009, Nature, 462, 1070).

There is a need in the art for novel inhibitors of EGFR. Such inhibitors would be useful for treating diseases caused by EGFR activation and constitutively active mutants. The present invention fulfills these needs.

SUMMARY OF THE INVENTION

The present invention provides an isolated peptide that interacts with a juxtamembrane segment of a protein and allosterically modulates activity of the protein. In one embodiment, the peptide interacts with a juxtamembrane segment of a protein and allosterically inhibits activity of the protein. In one embodiment, the peptide interacts with a juxtamembrane segment of a protein and allosterically activates activity of the protein. In one embodiment, the protein is a member of the epidermal growth factor receptor family.

In one embodiment, the peptide binds to an α-helix or coiled coil domain of EGFR. In one embodiment, the α-helix or coiled coil domain is selected from the group consisting of EGF α-helix or coiled coil domain, TGF α-helix or coiled coil domain, and a combination thereof. In one embodiment, the peptide allosterically modulates EGFR activation by modulating coiled coil formation.

In one embodiment, the peptide comprises one or more unnatural amino acids. In one embodiment, the peptide comprises one or more hydrocarbon staples between two or more amino acids. In one embodiment, the peptide comprises an amino acid sequence selected from the group consisting of SEQ ID NOs: 1-19. In one embodiment, the peptide comprises an amino acid sequence that is at least about 90% homologous to an amino acid sequence selected from the group consisting of SEQ ID NOs: 1-19.

The present invention provides a method for modulating activation of a protein having a juxtamembrane segment, the method comprising contacting the protein with a peptide that interacts with a juxtamembrane segment of a protein and allosterically modulates activity of the protein. In one embodiment, the peptide interacts with a juxtamembrane segment of a protein and allosterically inhibits activity of the protein. In one embodiment, the peptide interacts with a juxtamembrane segment of a protein and allosterically activates activity of the protein. In one embodiment, the protein is a member of the epidermal growth factor receptor family.

In one embodiment, the peptide binds to an α-helix or coiled coil domain of EGFR. In one embodiment, the an α-helix or coiled coil domain is selected from the group consisting of EGF an α-helix or coiled coil domain, TGF an α-helix or coiled coil domain, and a combination thereof. In one embodiment, the peptide allosterically modulates EGFR activation by modulating coiled coil formation.

In one embodiment, peptide comprises one or more unnatural amino acids. In one embodiment, the peptide comprises one or more hydrocarbon staples between two or more amino acids. In one embodiment, the peptide comprises an amino acid sequence selected from the group consisting of SEQ ID NOs: 1-19. In one embodiment, the peptide comprises an amino acid sequence that is at least about 90% homologous to an amino acid sequence selected from the group consisting of SEQ ID NOs: 1-19.

The present invention provides a method of treating or preventing a disease or condition in a subject in need thereof, wherein the disease or condition is associated with dysfunctional EGFR activity. The method comprises administering to the subject a therapeutically effective amount of a pharmaceutical composition comprising a peptide that interacts with a juxtamembrane segment of a protein and allosterically modulates activity of the protein, whereby administration of the composition to the subject treats or prevents the disease or condition in the subject.

In one embodiment, the peptide comprises an amino acid sequence selected from the group consisting of SEQ ID NOs: 1-19. In one embodiment, the peptide comprises an amino acid sequence that is at least about 90% homologous to an amino acid sequence selected from the group consisting of SEQ ID NOs: 1-19.

In one embodiment, the disease or condition is selected from the group consisting of cancer, an inflammatory disease, an autoimmune disease, an angiogenic disease, a renal disorder, and a cardiovascular disease.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2 is a schematic showing that peptide mimetics that target the juxtamembrane inhibit kinase activity in living cells.

FIG. 3 is a chart showing representative peptide mimetics.

FIG. 5 is a chart demonstrating that the activity of various peptide mimetics on cells that express EGFR.

FIG. 7 is a schematic demonstrating that other ErbB family members and other receptor tyrosine kinases can be modulated by allosteric inhibition.

FIG. 8 depicts the structure of $JM^{WT}$ (top) and $E1^{Alb}$ (bottom).

FIG. 9 depicts the structure of $E1^U$ (top) and $E2^U$ (bottom).

FIG. 10 depicts the structure of $E1^S$ (top) and $E2^S$ (bottom).

FIG. 11 depicts the structure of $E3^U$ (top) and $E4^U$ (bottom).

FIG. 13 depicts the structure of $T1^U$ (top) and $T2^U$ (bottom).

FIG. 14 depicts the structure of $T1^S$ (top) and $T2^S$ (bottom).

FIG. 16 depicts the structure of $T3^S$ (top) and $T4^S$ (bottom).

FIG. 17, comprising (FIG. 17A) Potential equilibria between EGFR monomers and dimers +/− growth factor (EGF) and allosteric inhibitors. (FIG. 17B) Helical wheel representation and sequences of hydrocarbon stapled peptides evaluated in example experiments presented herein. Z, X, and B represent (R)-2-(7'-octenyl)alanine ($R_8$), (S)-2-(4'-pentenyl)alanine ($S_5$), and (R)-2-(4'-pentenyl)alanine ($R_5$) respectively. Peptides constrained with a hydrocarbon staple are indicated with the superscript S ($E1^S$, for example).

DETAILED DESCRIPTION OF THE INVENTION

Figure 1:
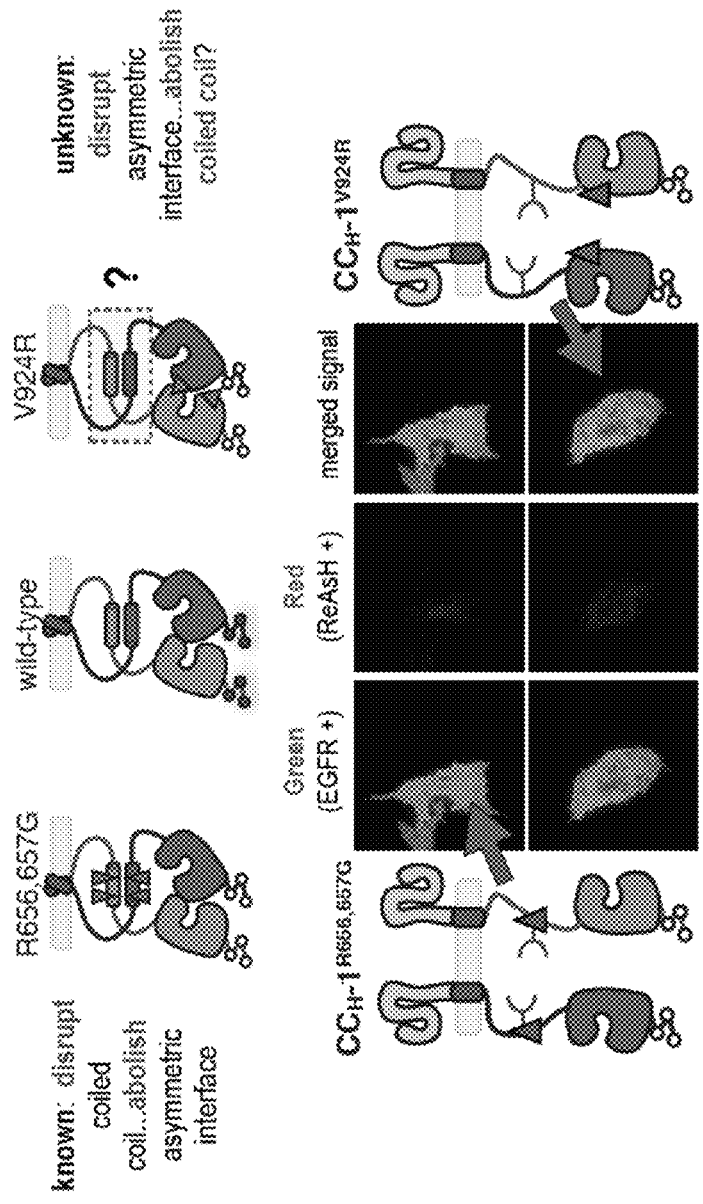
FIG. 1 is a schematic showing that the juxtamembrane segment is an allosteric regulator of kinase activity.

The present invention relates to a novel class of allosteric modulators that target a protein having a juxtamembrane segment. In one embodiment, the protein having a juxtamembrane segment includes, but is not limited to, the epidermal growth factor receptor family, receptor tyrosine kinases, and the like. In another embodiment, the allosteric modulator is a peptide mimetic that is capable of interacting with an α-helical or coiled coil domain of a protein. In some embodiments, the modulator is an inhibitor. In other embodiments, the modulator is an activator. Thus, in one embodiment, the present invention provides methods and compositions for modulating EGFR activity.

In some embodiments, the composition of the invention includes an allosteric inhibitor that inhibits EGFR activation wherein the inhibitor binds to an α-helical or coiled coil domain present in EGFR. In one embodiment, the composition of the invention includes an allosteric inhibitor that inhibits EGFR activation wherein the inhibitor binds the coiled coil interface formed when EGFR is stimulated with TGF-α (referred elsewhere herein as TGF coiled coil). In another embodiment, the composition of the invention includes an allosteric inhibitor that inhibits EGFR activation wherein the inhibitor binds the coiled coil interface formed when EGFR is stimulated with EGF (referred elsewhere herein as EGF coiled coil). In yet another embodiment, the composition of the invention includes an allosteric inhibitor that inhibits EGFR activation wherein the inhibitor binds to both coiled coil domains present in EGFR (e.g., the TGF coiled coil and the EGF coiled coil).

In other embodiments, the composition of the invention includes an allosteric activator that promotes EGFR activation wherein the activator binds to an α-helical or coiled coil domain present in EGFR. In one embodiment, the composition of the invention includes an allosteric activator that activates EGFR wherein the activator promotes the coiled coil interface formed when EGFR is stimulated with TGF-α (referred elsewhere herein as TGF coiled coil). In another embodiment, the composition of the invention includes an allosteric activator that activates EGFR wherein the activator promotes the coiled coil interface formed when EGFR is stimulated with EGF (referred elsewhere herein as EGF coiled coil). In yet another embodiment, the composition of the invention includes an allosteric activator that activates EGFR wherein the activator binds to both coiled coil domains present in EGFR (e.g., the TGF coiled coil and the EGF coiled coil).

In one embodiment, the invention provides an isolated peptide mimetic that interacts with an EGFR peptide and allosterically modulates activity of EGFR. In one embodiment, the isolated peptide mimetic allosterically modulates EGFR activation by binding to one or more α-helical or coiled coil domains present in EGFR. In such an embodiment, the one or more α-helical or coiled coil domains present in EGFR include at least one of EGF coiled coil and TGF coiled coil.

In certain embodiments, the peptide mimetic of the present invention comprises one or more unnatural amino acids. For example, in certain embodiments, the peptide mimetic comprises one or more unnatural amino acids which form a hydrocarbon staple, thereby forming a "stapled peptide." In one embodiment, the peptide mimetic comprises one or more unnatural amino acids with olefinic side chains (olefinic unnatural amino acids), which form a hydrocarbon staple by a olefin metathesis reaction.

In one embodiment, the invention provides a method for inhibiting EGFR activation. This method includes the step of contacting an EGFR with a peptide mimetic of the invention, wherein the peptide mimetic is an allosteric inhibitor. In another embodiment, the invention provides a method for activating EGFR activation. This method includes the step of contacting an EGFR with a peptide mimetic of the invention, wherein the peptide mimetic is an allosteric inhibitor.

In another embodiment, the invention provides a method of treating a disease or disorder associated with EGFR activation. In one embodiment, the disease or disorder associated with EGFR activation is characterized by excessive activation of EGFR. In another embodiment, the invention provides a method of treating a disease or disorder associated with EGFR inactivation. In one embodiment, the disease or disorder associated with EGFR inactivation is characterized by deficient activation of EGFR.

In one embodiment, the invention provides a pharmaceutical composition which includes one or more isolated peptide mimetics In one embodiment, the one or more peptide mimetic is combined with at least one pharmaceutically acceptable carrier.

DEFINITIONS

As used herein, each of the following terms has the meaning associated with it in this section. Unless defined otherwise, all technical and scientific terms used herein generally have the same meaning as commonly understood by one of ordinary skill in the art to which this invention belongs.

The articles "a" and "an" are used herein to refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20%, ±10%, ±5%, ±1%, or ±0.1% from the specified value, as such variations are appropriate to perform the disclosed methods.

An "allosteric" mechanism refers to a mechanism of action in which a molecule combines with a site on the protein other than the active site. In an exemplary embodiment, the combination results in a change in the protein's conformation, e.g., at or proximate to the active site.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A cancer "characterized by excessive activation" of EGFR is one in which the extent of EGFR activation in cancer cells significantly exceeds the level of activation of that receptor in non-cancerous cells of the same tissue type. Such excessive activation may result from overexpression of EGFR and/or greater than normal levels of an EGFR ligand available for activating the EGFR receptor in the cancer cells. Overexpression of EGFR may refer to greater than normal levels of EGFR protein or mRNA. Excessive activation of EGFR may cause and/or be caused by the malignant state of a cancer cell.

A "dimer" is a molecule that comprises two simpler, often identical molecules. When both components (also called "subunits") of a dimer are identical to each other, the dimer can also be referred to as a "homodimer," while a dimer comprising non-identical subunits can be referred to as a "heterodimer." An "EGFR dimer" is a dimer in which at least one subunit corresponds to a member of the ErbB receptor family. "EGFR dimer," "EGFR molecule" and "EGFR protein" can be used interchangeably.

The term "amino acid" refers to a molecule containing both an amino group and a carboxyl group. Suitable amino acids include, without limitation, both the D- and L-isomers of the 20 common naturally occurring amino acids found in peptides as well as the naturally occurring and non-naturally occurring amino acids including beta-amino acids and α,α disubstituted amino acids, prepared by organic synthesis or other metabolic routes and that can be applied for specialized uses such as increasing chemical diversity, functionality, binding capacity, structural mimesis, and stability. As used herein, amino acids are represented by the full name thereof, by the three-letter code as well as the one-letter code corresponding thereto:

| Full Name | 3-Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

"EGFR" refers to Epidermal Growth Factor Receptor. All EGFR family members are encompassed by the present invention. As used herein, unless otherwise identified, the term "EGFR" refers to any receptor protein tyrosine kinase belonging to the ErbB receptor family, including without limitation HER1, HER2, HER3, HER4, as well as any other members of this family to be identified in the future. The EGFR receptor will generally comprise an extracellular domain, which may bind an EGFR ligand; a lipophilic transmembrane domain; a conserved intracellular tyrosine kinase domain; and a carboxyl-terminal signaling domain harboring several tyrosine residues which can be phosphorylated. EGFR may be a "native sequence" EGFR or an "amino acid sequence variant" thereof.

An "EGFR molecule" encompasses the amino acid sequence encoding for EGFR. The term also encompasses less than complete fragments of the amino acid sequence, as well as proteins, polypeptides and polypeptide fragments derived from a full-length EGFR protein.

An "EGFR encoding nucleic acid" encompasses the nucleotide sequence encoding for EGFR. The term also encompasses less than full-length nucleotide sequences, as well sequences which have been altered, e.g., mutated with insertions, deletions, and substitutions, and sequences which have been inserted into delivery vehicles, such as recombinant expression vectors.

The "activity" of a polypeptide or protein refers to a functional property associated with that molecule. For example, "EGFR activity" can refer to the tyrosine kinase activity of the molecule as well as the process of dimerization upon binding a ligand. The specific activity associated with a polypeptide or protein can also be identified through a description of a functional process, e.g., phosphorylation.

The terms "EGFR protein" and "EGFR polypeptide" are used interchangeably and encompass full length, wildtype, fragment, variant and mutant EGFR molecules. The terms encompass polypeptides having an amino acid sequence which substantially corresponds to at least one 10 to 50 residue (e.g., 10, 20, 25, 30, 35, 40, 45, 50) amino acid fragment and/or a sequence homologous to a known EGFR or group of EGFRs, wherein the EGFR polypeptide has homology of at least 80%, such as at least 81, 82, 83, 84, 85, 86, 87, 88, 89, 90, 91, 92, 93, 94, 95, 96, 97, 98, 99 or 100% homology, to the sequence of said known EGFR or group of EGFRs, and exhibits EGFR activity. Encompassed in the present invention is an EGFR polypeptide which is not naturally occurring or is naturally occurring but is in a purified or isolated form which does not occur in nature.

As used herein, the terms "effective amount" and "pharmaceutically effective amount" refer to a nontoxic but sufficient amount of an agent or drug to provide the desired biological result. That result can be reduction and/or alleviation of the signs, symptoms, or causes of a disease or disorder, imaging or monitoring of an in vitro or in vivo system (including a living organism), or any other desired alteration of a biological system. An appropriate effective amount in any individual case may be determined by one of ordinary skill in the art using routine experimentation.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, the term "fragment," as applied to a protein or peptide, refers to a subsequence of a larger protein or peptide. A "fragment" of a protein or peptide may be at least about 10 amino acids in length; for example, at least about 50 amino acids in length; more preferably, at least about 100 amino acids in length; even more preferably, at least about 200 amino acids in length; particularly preferably, at least about 300 amino acids in length; and most preferably, at least about 400 amino acids in length.

As used herein, the term "homologous" refers to the subunit sequence similarity between two polymeric molecules, e.g., between two nucleic acid molecules, such as two DNA molecules or two RNA molecules, or between two protein molecules. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. As used herein, "homology" is used synonymously with "identity."

As used herein, the term "hydrocarbon stapling," refers to a process for stably cross-linking a peptide having at least two amino acids that helps to conformationally bestow the native secondary structure of that peptide. Hydrocarbon stapling promotes or maintains a helical secondary structure in a peptide predisposed to have a helical secondary structure, e.g., alpha-helical secondary structure, to attain or maintain its native alpha-helical conformation.

An "individual," "patient" or "subject," as those terms are used herein, includes a member of any animal species including, but are not limited to, birds, humans and other primates, and other mammals including commercially relevant mammals such as cattle, pigs, horses, sheep, cats, and dogs. Preferably, the subject is a human.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

As used herein, the term "modulate," and grammatical variants thereof, refers to an increase, decrease, or other alteration of any or all biological activities or properties of an EGFR family member. Similarly, the term "modulator" refers to a compound (e.g., an antibody, antibody derivative, peptide, peptide mimetic, small molecule, polymer, etc.) that in some embodiments inhibits a biological activity of an EGFR family member and in other embodiments activates a biological activity of an EGFR family member. "EGFR inhibitor" refers to a substance that acts by inhibiting, blocking, decreasing, antagonizing, or otherwise reducing EGFR activity in cells and tissues. "EGFR activator" refers to a substance that acts by promoting, agonizing, or otherwise increasing EGFR activity in cells and tissues.

The term "mutant EGFR" encompasses naturally occurring mutants and mutants created chemically and/or using recombinant techniques. "Mutant EGFR" and "mutant EGFR molecules" can be used interchangeably.

As used herein, the terms "protein," "peptide" and "polypeptide" are used interchangeably, and refer to a compound comprised of natural or unnatural amino acid residues covalently linked by peptide bonds. The term "peptide bond" means a covalent amide linkage formed by loss of a molecule of water between the carboxyl group of one amino acid and the amino group of a second amino acid. A protein or peptide must contain at least two amino acids, and no limitation is placed on the maximum number of amino acids that may comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Proteins" include, for example, biologically active fragments, substantially homologous proteins, oligopeptides, homodimers, heterodimers, variants of proteins, modified proteins, derivatives, analogs, and fusion proteins, among others. The proteins include natural proteins, recombinant proteins, synthetic proteins, or a combination thereof. A protein may be a receptor or a non-receptor.

As used herein, the term "substantially the same" amino acid sequence is defined as a sequence with at least 70%, preferably at least about 80%, more preferably at least about 85%, more preferably at least about 90%, even more preferably at least about 95%, and most preferably at least 99% homology with another amino acid sequence, as determined by the FASTA search method in accordance with Pearson & Lipman, 1988, Proc. Natl. Inst. Acad. Sci. USA 85:2444-48.

By the term "specifically bind" or "specifically binds," as used herein, is meant that a first molecule preferentially binds to a second molecule, but does not necessarily bind only to that second molecule.

"Isolated" means altered or removed from the natural state through the actions of a human being. For example, a nucleic acid or a protein naturally present in a living animal is not "isolated," but the same nucleic acid or protein partially or completely separated from the coexisting materials of its natural state is "isolated." An isolated nucleic acid or protein can exist in substantially purified form, or can exist in a non-native environment such as, for example, a host cell.

As used herein, the term "pharmaceutically acceptable" refers to a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

As used herein, the term "pharmaceutical composition" refers to a mixture of at least one compound of the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration. As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention is based in part on the discovery of novel peptide mimetics that kill lung cancer cells that express wild type EGFR or L858R EGFR or L858R/T790M EGFR. Accordingly, the invention provides compositions and methods for modulating the activity of a protein having a juxtamembrane segment. In one embodiment, the protein having a juxtamembrane segment includes but is not limited to the epidermal growth factor receptor family, receptor tyrosine kinases, and the like.

In one embodiment, the modulator of the invention is an allosteric modulator. In another embodiment, the allosteric modulator is a peptide mimetic that is capable of interacting with at least one α-helical or coiled coil domain of a protein.

Composition

In one embodiment, the present invention provides compositions for the modulation of the activity of a protein having a juxtamembrane segment, including for example members of the epidermal growth factor (EGF) family and receptor tyrosine kinases (RTK).

In one embodiment, the invention provides novel allosteric inhibitors of EGFR. In one embodiment, the invention provides inhibitors which act by preventing activation of EGFR. In a still further embodiment, the inhibitors bind to an α-helical or coiled coil domain and inhibit coiled coil formation. In one embodiment, the inhibitors prevent formation of a dimer interface between EGFR monomers. In such a mechanism of inhibition, the EGFR molecule retains a basal level of activity but is inhibited from activating, i.e., is prevented from prompting the signal transduction cascade that would normally develop upon binding of a ligand to the extracellular activation loop of EGFR (also referred to herein as the "ligand binding region of EGFR"). In one embodiment, the present invention provides inhibitors which bind to one or more coiled coils domains present in EGFR including but is not limited to EGF coiled coil and TGF coiled coil, thereby preventing formation of the dimer interface, which in turn prevents one or more of activation of EGFR, decoding and relaying extracellular signals to the cytosol.

In another embodiment, the invention provides novel allosteric activators of EGFR. In one embodiment, the invention provides activators which act by promoting activation of EGFR. In a still further embodiment, the activators bind to an α-helical or coiled coil domain and promote coiled coil formation. In one embodiment, the activators promote formation of a dimer interface between EGFR monomers. In one embodiment, the present invention provides activators which bind to one or more coiled coils domains present in EGFR including but is not limited to EGF coiled coil and TGF coiled coil, thereby promoting formation of the dimer interface, which in turn promotes one or more of activation of EGFR, decoding and relaying extracellular signals to the cytosol.

In one embodiment, the composition comprises a peptide mimetic comprising one or more unnatural or non-natural amino acids. Non-natural amino acids include, but are not limited to, the D-amino acids, 2,4-diaminobutyric acid, α-amino isobutyric acid, 2-aminoisobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general.

In one embodiment, the peptide mimetic of the invention comprises one or more α-aminoisobutyric acid residues. In certain instances, inclusion of one or more α-aminoisobutyric acid residues promotes helical formation of the peptide.

In certain embodiments, the peptide mimetic of the invention comprises one or more unnatural amino acids with olefinic side chains. Specific examples of unnatural amino acids with olefinic side chains include, but is not limited to (S)-2-(7'-octenyl)alanine, (R)-2-(7'-octenyl)alanine, (S)-2-(4'-pentenyl)alanine, and (R)-2-(4'-pentenyl)alanine.

In one embodiment, the peptide mimetic comprises one or more unnatural amino acids which form a hydrocarbon staple. Hydrocarbon stapling is described in U.S. Publication Nos. 2005/0250680, 2010/0234563, 2007/0197772, 2006/0008848, 2006/0014675; U.S. Pat. Nos. 7,723,469, 7,192,713, and 7,084,244; International Publication Nos. WO 2009/108261 and WO 2010/148335; and Kawamoto, S. A. et al, J. Med. Chem. 55, 1137-1146 (2012); Mahon, A. B. and Arora, P. S., Chem. Commun 48, 1416-1418 (2012); and Chapman, R. N. et al, J. Am. Chem. Soc. 126, 12252-3 (2004), which are incorporated herein by reference in their entirety.

The peptide α-helix participates in critically important protein interactions by presenting specific amino acid residues in an ordered and precise arrangement over a relatively large contact surface area (Chittenden, T., et al, Embo Journal, 1995. 14(22): p. 5589-5596; Kussie, P. H., et al. Science, 1996. 274(5289): p. 948-953; Ellenberger, T. E., et al, Cell, 1992. 71(7): p. 1223-1237). Alpha-helical domains and other protein structural features are frequently stabilized by scaffold sequences in the remainder of the protein, which facilitate the formation and/or maintenance of a helical structure, e.g., an α-helical structure. When taken out of context, α-helical peptide motifs can unfold, leading to loss of biological activity. Critical challenges in developing α-helical peptides include promoting and/or maintaining their natural <x-helical structure and preparing peptides that can resist proteolytic, acid and thermal degradation, and thereby remain intact in vivo.

Hydrocarbon stapling refers to a process for stably cross-linking a polypeptide via at least two substituted amino acids (or a non-native linkage, e.g., carbon-carbon, from two natural amino acids) that helps to conformationally bestow the native secondary structure of that polypeptide. Hydrocarbon stapling promotes and maintains an alpha-helical secondary structure in peptides that thermodynamically favor an alpha-helical structure. In certain instances, this secondary structure increases resistance of the polypeptide to proteolytic cleavage and heat, and also may increase hydrophobicity. Accordingly, the hydrocarbon stapled (structurally constrained, e.g., crosslinked) peptides described herein have improved biological activity relative to a corresponding non-hydrocarbon stapled (not structurally constrained) polypeptide.

Hydrocarbon staples suitable for the present peptide mimetic are described herein and in U.S. Publication Nos. 2005/0250680, 2010/0234563, 2007/0197772, 2006/0008848, 2006/0014675; U.S. Pat. Nos. 7,723,469, 7,192, 713, and 7,084,244; International Publication Nos. WO 2009/108261) and WO 2010/148335; and Kawamoto, S. A. et al, J. Med. Chem. 55, 1137-1146 (2012); Mahon, A. B. and Arora, P. S., Chem. Commun 48, 1416-1418 (2012); and Chapman, R. N. et al., J. Am. Chem. Soc. 126, 12252-3 (2004), which are incorporated by reference in their entirety. Hydrocarbon stapling allows a peptide, predisposed to have a helical secondary structure, to maintain its native helical conformation and increase its stability and efficacy. In one embodiment, the stapled peptide has at least 10%, 20%, 30%, 35%, 40%, 45%, 50%, 60%, 70%, 80%, or 90% or more helicity in an aqueous solution as determined by circular dichroism. Assays for determining circular dichroism are known in the art and described herein.

The hydrocarbon stapled peptides include a tether (linkage) between two amino acids, in which the tether significantly enhances the helical secondary structure of the peptide. Generally, the tether extends across the length of one or two helical turns (i.e., 3, 4 or 7 amino acids). Accordingly, amino acids positioned at i and i+3; i and i+4; or i and i+7 are ideal candidates for chemical modification and cross-linking. Thus, any of the amino acid residues of the peptides of the invention may be tethered (e.g., cross-linked) in conformity with the above. Suitable tethers are described herein and in U.S. Publication Nos. 2005/0250680, 2010/0234563, 2007/0197772, 2006/0008848, 2006/0014675; U.S. Pat. Nos. 7,723,469, 7,192,713, and 7,084,244; International Publication Nos. WO 2009/108261 and WO 2010/148335; and Kawamoto, S. A. et al., J. Med. Chem. 55, 1137-1146 (2012); Mahon, A. B. and Arora, P. S., Chem. Commun 48, 1416-1418 (2012); and Chapman, R. N. et al., J. Am. Chem. Soc. 126, 12252-3 (2004). It is understood that tethers such as hydrocarbon staples can be positioned at other intervals to promote helical variants (e.g., with different pitches, angles, or residues and fractions thereof per turn) or structures other than helices.

In a further embodiment, the hydrocarbon staple(s) is positioned so as to link a first amino acid (i) and a second amino acid (i+3) which is 3 amino acids downstream of the first amino acid. In another embodiment, the hydrocarbon staple hnks a first amino acid (i) and a second amino acid (i+4) which is 4 amino acids downstream of the first amino acid. In yet another embodiment, the hydrocarbon staple hnks a first amino acid (i) and a second amino acid (i+7) which is 7 amino acids downstream of the first amino acid.

The hydrocarbon stapled peptide includes one or more tethers (linkages) between two unnatural amino acids (or a non-native linkage, e.g., carbon-carbon, from two natural amino acids), which tether significantly enhances the helical secondary structure of the peptide. Generally, to promote a helical structure, the tether extends across the length of one or two helical turns (i.e., about 3, 4, or 7 amino acids). Accordingly, amino acids positioned at i and i+3; i and i+4; or i and i+7 are ideal candidates for chemical modification and cross-linking. Thus, for example, where a peptide has the sequence . . . XI, X2, X3, X4, X5, X6, X7, X8, X9 . . . , and the amino acid X is independently selected for each position, cross-links between XI and X4, or between XI and X5, or between XI and X8 are useful as are cross-links between X2 and X5, or between X2 and X6, or between X2 and X9, etc. The use of multiple cross-links (e.g., 2, 3, 4 or more) is also contemplated. The use of multiple cross-links is effective at stabilizing and optimizing the peptide, especially with increasing peptide length. The use of "stitched" cross-links has also been achieved whereby double linkages are made from a common origin (e.g., XI, X5, and X9, where X5 is the anchor point for both staples). Thus, the invention encompasses the incorporation of one or more crosslinks within the peptide sequence. The use of multiple cross-links is effective at stabilizing and optimizing the peptide, especially with increasing peptide length. Thus, the invention encompasses the incorporation of one or more crosslinks within a peptide sequence, including stitched crosslinks in which two staples arise from a common origin.

While hydrocarbon staples or tethers have been described, other tethers are also envisioned. For example, the tether can include one or more of an ether, thioether, ester, amine, or amide moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid.

It is further envisioned that the length of the tether can be varied. For instance, a shorter length of tether can be used where it is desirable to provide a relatively high degree of constraint on the secondary structure, whereas, in some instances, it is desirable to provide less constraint on the secondary structure, and thus a longer tether may be desired. It is further understood that the insertion of the tether at a site or in an amino acid sequence when the amino acid sequence has no tendency to form a helix will not result in helix formation.

Additionally, while examples of tethers spanning from amino acids i to i+3, i to i+4; and i to i+7 have been described in order to provide a tether that is primarily on a single face of the alpha helix, the tethers can be synthesized to span any combinations of numbers of amino acids to promote and/or maintain the structures other than alpha helices.

In one embodiment, the stapled peptide of the invention comprises a staple formed between two unnatural amino acids, where the unnatural amino acids comprise an olefinic side chain. Exemplary unnatural amino acids which comprise an olefinic side chain include, but are not limited to, (S)-2-(7'-octenyl)alanine, (R)-2-(7'-octenyl)alanine, (S)-2-(4'-pentenyl)alanine, and (R)-2-(4'-pentenyl)alanine. In certain embodiments, the staple is formed by an olefin metathesis reaction. However, in certain embodiments, the peptide comprises one or more unnatural amino acid having an olefinic side chain, but is "unstapled" meaning that a staple or cross-link is not formed between the unnatural amino acids. For example, it is shown herein that certain peptides modulate EGFR function in its stapled or unstapled In one embodiment, the allosteric modulator of the invention comprises a peptide comprising the amino acid sequence of VRKRTLRRLLQERELVE (SEQ ID NO: 1; $JM^{WT}$).

In one embodiment, the allosteric modulator of the invention comprises a peptide comprising the amino acid sequence of VRKRX1LRRLLQX2RELVE (SEQ ID NO: 2), where X1 and X2 are amino acids which form a staple. For example, in one embodiment, the allosteric modulator of the invention comprises a peptide comprising the amino acid sequence of VRKRZLRRLLQXRELVE (SEQ ID NO: 3; E1), where Z is (R)-2-(7'-octenyl)alanine and X is (S)-2-(4'-pentenyl)alanine. In one embodiment, the allosteric modulator of the invention comprises a peptide comprising the amino acid sequence of VRKRXLRRLLQXRELVE (SEQ ID NO: 18; $E1^{Aib}$), where X=α-aminoisobutyric acid. In one embodiment, the allosteric modulator of the invention comprises a peptide comprising the amino acid sequence of VRKRZARRAAQXRELVE (SEQ ID NO: 19; $E1_{AL}$), where Z is (R)-2-(7'-octenyl)alanine and X is (S)-2-(4'-pentenyl)alanine.

In one embodiment, the allosteric modulator of the invention comprises a peptide comprising the amino acid sequence of VRKRTLRX1LLQX2RELVE (SEQ ID NO: 4), where X1 and X2 are amino acids which form a staple. For example, in one embodiment, the allosteric modulator of the invention comprises a peptide comprising the amino acid sequence of VRKRTLRXLLQXRELVE (SEQ ID NO: 5; E2), where X is (S)-2-(4'-pentenyl)alanine.

In one embodiment, the allosteric modulator of the invention comprises a peptide comprising the amino acid sequence of VRKRTLX1RLLX2ERELVE (SEQ ID NO: 6), where X1 and X2 are amino acids which form a staple. For example, in one embodiment, the allosteric modulator of the invention comprises a peptide comprising the amino acid sequence of VRKRTLXRLLXERELVE (SEQ ID NO: 7; E3), where X is (S)-2-(4'-pentenyl)alanine.

In one embodiment, the allosteric modulator of the invention comprises a peptide comprising the amino acid sequence of VRKRTLRX1LLX2ERELVE (SEQ ID NO: 8), where X1 and X2 are amino acids which form a staple. For example, in one embodiment, the allosteric modulator of the invention comprises a peptide comprising the amino acid sequence of VRKRTLRBLLXERELVE (SEQ ID NO: 9; E4), where B is (R)-2-(4'-pentenyl)alanine and X is (S)-2-(4'-pentenyl)alanine.

In one embodiment, the allosteric modulator of the invention comprises a peptide comprising the amino acid sequence of VRKRTX1RRLX2QERELVE (SEQ ID NO: 10), where X1 and X2 are amino acids which form a staple. For example, in one embodiment, the allosteric modulator of the invention comprises a peptide comprising the amino acid sequence of VRKRTXRRLXQERELVE (SEQ ID NO: 11; T1), where X is (S)-2-(4'-pentenyl)alanine.

In one embodiment, the allosteric modulator of the invention comprises a peptide comprising the amino acid sequence of VRKRTLRRLX1QERX2LVE (SEQ ID NO: 12), where X1 and X2 are amino acids which form a staple. For example, in one embodiment, the allosteric modulator of the invention comprises a peptide comprising the amino acid sequence of VRKRTLRRLXQERXLVE (SEQ ID NO: 13; T2), where X is (S)-2-(4'-pentenyl)alanine.

In one embodiment, the allosteric modulator of the invention comprises a peptide comprising the amino acid sequence of VRKRTX1RRX2LQERELVE (SEQ ID NO: 14), where X1 and X2 are amino acids which form a staple. For example, in one embodiment, the allosteric modulator of the invention comprises a peptide comprising the amino acid sequence of VRKRTBRRXLQERELVE (SEQ ID NO: 15; T3), where B is (R)-2-(4'-pentenyl)alanine and X is (S)-2-(4'-pentenyl)alanine.

In one embodiment, the allosteric modulator of the invention comprises a peptide comprising the amino acid sequence of VRKRX1LRRX2LQERELVE (SEQ ID NO:

16), where X1 and X2 are amino acids which form a staple. For example, in one embodiment, the allosteric modulator of the invention comprises a peptide comprising the amino acid sequence of VRKRXLRRXLQERELVE (SEQ ID NO: 17; T4), where X is (S)-2-(4'-pentenyl)alanine.

In one embodiment, the peptide mimetic of the invention comprises a peptide having at least 75% homology with a peptide having an amino acid sequence as set forth in SEQ ID NOs: 1-19. In one embodiment, the peptide mimetic of the invention comprises a peptide having at least 80% homology with a peptide having an amino acid sequence set forth in SEQ ID NOs: 1-19. In one embodiment, the peptide mimetic of the invention comprises a peptide having at least 85% homology with a peptide having an amino acid sequence set forth in SEQ ID NOs: 1-19. In one embodiment, the peptide mimetic of the invention comprises a peptide having at least 90% homology with a peptide having an amino acid sequence set forth in SEQ ID NOs: 1-19. In one embodiment, the peptide mimetic of the invention comprises a peptide having at least 95% homology with a peptide having an amino acid sequence set forth in SEQ ID NOs: 1-19. In one embodiment, the peptide mimetic of the invention comprises a peptide having at least 99% homology with a peptide having an amino acid sequence set forth in SEQ ID NOs: 1-19. In a further embodiment, the peptide mimetics of the invention comprise D-, L-, and unnatural isomers of amino acids.

Included in the invention are nucleic acid sequences that encode the peptide mimetics of the invention. In one embodiment, the invention includes nucleic acid sequences corresponding to the amino acid sequences listed in any one of having an amino acid sequence set forth in SEQ ID NOs 1-19. Accordingly, subclones of a nucleic acid sequence encoding a peptide mimetic of the invention can be produced using conventional molecular genetic manipulation for subcloning gene fragments, such as described by Sambrook et al., Molecular Cloning: A Laboratory Manual, Cold Springs Laboratory, Cold Springs Harbor, N.Y. (2012), and Ausubel et al. (ed.), Current Protocols in Molecular Biology, John Wiley & Sons (New York, N.Y.) (1999 and preceding editions), each of which is hereby incorporated by reference in its entirety. The subclones then are expressed in vitro or in vivo in bacterial cells to yield a smaller protein or polypeptide that can be tested for a particular activity.

In addition, chemical synthesis can also be employed using techniques well known in the chemistry of proteins such as solid phase synthesis or synthesis in homogenous solution.

Variants of suitable peptides of the invention can also be expressed. Variants may be made by, for example, the deletion, addition, or alteration of amino acids that have either (i) minimal influence on certain properties, secondary structure, and hydropathic nature of the polypeptide or (ii) substantial effect on one or more properties of the peptide mimetics of the invention.

Variants of the peptides of the invention can also be fragments of the peptides of the invention that include one or more deletion, addition, or alteration of amino acids of the peptides having an amino acid sequence set forth in SEQ ID NOs: 1-19. The substituted or additional amino acids can be either L-amino acids, D-amino acids, or modified amino acids. Whether a substitution, addition, or deletion results in modification of the activity of the peptide may depend, at least in part, on whether the altered amino acid is conserved. Conserved amino acids can be grouped either by molecular weight or charge and/or polarity of R groups, acidity, basicity, and presence of phenyl groups, as is known in the art.

Variants may also include, for example, a peptide conjugated to a linker or other sequence for ease of synthesis, purification, identification, or therapeutic use (i.e., delivery) of the peptide.

The variants of the peptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the peptide is an alternative splice variant of the peptide of the present invention, (iv) fragments of the peptides and/or (v) one in which the peptide is fused with another peptide, such as a leader or secretory sequence or a sequence which is employed for purification (for example, His-tag) or for detection (for example, Sv5 epitope tag). The fragments include peptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two peptides is determined by comparing the amino acid sequence and its conserved amino acid substitutes of one peptide to a sequence of a second peptide. Variants are defined to include peptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to bind to ubiquitin or to a ubiquitylated protein. The present invention includes amino acid sequences that are at least 60%, 65%, 70%, 72%, 74%, 76%, 78%, 80%, 90%, or 95° A similar or identical to the original amino acid sequence. The degree of identity between two peptides is determined using computer algorithms and methods that are widely known for the persons skilled in the art. The identity between two amino acid sequences is preferably determined by using the BLASTP algorithm (BLAST Manual, Altschul, S., et al., NCBI NLM NIH Bethesda, Md. 20894, Altschul, S., et al., J. Mol. Biol. 215: 403-410 (1990)).

The peptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or Xenopus egg extracts (U.S. Pat. No. 6,103,489) to a standard translation reaction.

The peptides of the invention may include unnatural amino acids formed by post-translational modification or by introducing unnatural amino acids during translation. A variety of approaches are available for introducing unnatural amino acids during protein translation. By way of example, special tRNAs, such as tRNAs which have suppressor properties, suppressor tRNAs, have been used in the process of site-directed non-native amino acid replacement (SNAAR). In SNAAR, a unique codon is required on the mRNA and the suppressor tRNA, acting to target a non-native amino acid to a unique site during the protein synthesis (described in WO90/05785). However, the suppressor tRNA must not be recognizable by the aminoacyl tRNA synthetases present in the protein translation system. In certain cases, a non-native amino acid can be formed after the tRNA molecule is aminoacylated using chemical reactions which specifically modify the native amino acid and do not significantly alter the functional activity of the aminoacylated tRNA. These reactions are referred to as post-aminoacylation modifications. For example, the epsilon-amino group of the lysine linked to its cognate tRNA (tRNA$_{LYS}$), could be modified with an amine specific photoaffinity label.

A peptide mimetic of the invention may be conjugated with other molecules, such as proteins, to prepare fusion proteins. This may be accomplished, for example, by the synthesis of N-terminal or C-terminal fusion proteins provided that the resulting fusion protein retains the functionality of the peptide inhibitor.

Cyclic derivatives of the peptides or chimeric proteins of the invention are also part of the present invention. Cyclization may allow the peptide or chimeric protein to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

In other embodiments, the subject peptide modulator therapeutic agents are peptidomimetics of the peptide modulators. Peptidomimetics are compounds based on, or derived from, peptides and proteins. The peptidomimetics of the present invention typically can be obtained by structural modification of a known peptide modulator sequence using unnatural amino acids, conformational restraints, isosteric replacement, and the like. The subject peptidomimetics constitute the continuum of structural space between peptides and non-peptide synthetic structures; peptidomimetics may be useful, therefore, in delineating pharmacophores and in helping to translate peptides into nonpeptide compounds with the activity of the parent peptide inhibitors.

Moreover, as is apparent from the present disclosure, mimetopes of the subject peptide modulators can be provided. Such peptidomimetics can have such attributes as being non-hydrolyzable (e.g., increased stability against proteases or other physiological conditions which degrade the corresponding peptide), increased specificity and/or potency, and increased cell permeability for intracellular localization of the peptidomimetic. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988, p 123), C-7 mimics (Huffman et al. in Peptides: Chemistry and Biologyy, G. R. Marshall ed., ESCOM Publisher: Leiden, Netherlands, 1988, p. 105), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), β-aminoalcohols (Gordon et al. (1985) Biochem Biophys Res Commun 126:419; and Dann et al. (1986) Biochem Biophys Res Commun 134:71), diaminoketones (Natarajan et al. (1984) Biochem Biophys Res Commun 124:141), and methyleneamino-modified (Roark et al. in Peptides: Chemistry and Biology, G. R. Marshall ed., ESCOM Publisher: Leiden, Netherlands, 1988, p 134). Also, see generally, Session III: Analytic and synthetic methods, in Peptides: Chemistry and Biology, G. R. Marshall ed., ESCOM Publisher: Leiden, Netherlands, 1988).

In addition to a variety of side chain replacements which can be carried out to generate the peptidomimetics, the present invention specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

Moreover, other examples of mimetopes include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof. A mimetope can be obtained by, for example, screening libraries of natural and synthetic compounds for compounds capable of binding to the peptide inhibitor. A mimetope can also be obtained, for example, from libraries of natural and synthetic compounds, in particular, chemical or combinatorial libraries (i.e., libraries of compounds that differ in sequence or size but that have the same building blocks). A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modelling, the predicted mimetope structures can then be produced by, for example, chemical synthesis, recombinant DNA technology, or by isolating a mimetope from a natural source (e.g., plants, animals, bacteria and fungi).

A peptide mimetic of the invention may be synthesized by conventional techniques. For example, the peptide modulators may be synthesized by chemical synthesis using solid phase peptide synthesis. These methods employ either solid or solution phase synthesis methods (see for example, J. M. Stewart, and J. D. Young, Solid Phase Peptide Synthesis, 2$^{nd}$ Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis.)

Peptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors. (see Christian et al 1992, J. Mol. Biol. 227:711; Devlin et al, 1990 Science 249:404; Cwirla et al 1990, Proc. Natl. Acad, Sci. USA, 87:6378). Libraries may also be constructed by concurrent synthesis of overlapping peptides (see U.S. Pat. No. 4,708,871).

The peptides of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

Methods

In one aspect, the compounds of the present invention are useful as allosteric modulators, particularly as allosteric modulators of proteins having a juxtamembrane segment, more particularly as allosteric modulators of epidermal growth factor receptor family, receptor tyrosine kinases, and the like. In some embodiments, the modulators are inhibitors. In other embodiments, the modulators are activators.

The present invention includes a method of treating or preventing a disease or condition in a subject in need thereof, wherein the disease or condition is associated with dysfunctional EGFR regulation. The method comprises administering to the subject a therapeutically effective amount of a pharmaceutical composition comprising a modulator peptide or peptide-containing moiety, wherein the modulator peptide or peptide-containing moiety comprises any of the compounds described herein, including a peptide comprising an amino acid sequence set forth in one of SEQ ID NOs: 1-19. as well as fragments, mutants, variants, and derivatives thereof, whereby administration of the composition to the subject treats or prevents the disease or condition in the subject.

As contemplated herein, such diseases or conditions may include, without limitation, diseases or conditions associated with too much or too little EGFR activity. An example of a disease or condition associated with activation of EGFR is one in which the extent of EGFR activation in a cell significantly exceeds the level of activation of EGFR in an otherwise healthy cells of the same tissue type. Such excessive activation may result from overexpression of EGFR and/or greater than normal levels of an EGFR ligand available for activating the EGFR receptor in the cells. Overexpression of EGFR may refer to greater than normal levels of EGFR protein or mRNA. Another example of a disease or condition associated with activation of EGFR is one in which the extent of EGFR activation in a cell significantly fails to reach the level of activation of EGFR in an otherwise healthy cells of the same tissue type. Such insufficient activation may result from underexpression of EGFR and/or less than normal levels of an EGFR ligand available for activating the EGFR receptor in the cells. Underexpression of EGFR may refer to lesser than normal levels of EGFR protein or mRNA.

An example of a disease or condition associated with activation of EGFR is cancer. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

In one embodiment, the compounds of the present invention are useful for the treatment of diseases or disorders in which aberrant expression of ligand/receptor interactions or activation or signaling events related to EGFR are involved. Such disorders may include those of neuronal, glial, astrocytal, hypothalamic, and other glandular, macrophagal, epithelial, stromal, and blastocoelic nature in which aberrant function, expression, activation or signaling of EGFR is involved. In an additional aspect, the compounds of the present invention may have therapeutic utility in inflammatory, angiogenic and immunologic disorders involving both identified and as yet unidentified EGFRs and other tyrosine kinases that are inhibited by the compounds of the present invention.

In one embodiment, the invention provides a method for the treatment of abnormal cell growth in a mammal which comprises administering to said mammal an amount of a compound or composition, or a pharmaceutically acceptable salt, solvate or prodrug thereof, that is effective in treating abnormal cell growth. This treatment can in an exemplary embodiment be administered in combination with another anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens. In one embodiment, the invention provides a pharmaceutical composition for treating abnormal cell growth wherein the composition includes a compound which inhibits EGFR activation, or a pharmaceutically acceptable salt, solvate or prodrug thereof, that is effective in treating abnormal cell growth, and another anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

EGFR is often overexpressed in cancer. (Mendelsohn et al., (2006) Semin Oncol. 33(4):369-85). Arthritis, hypersecretory respiratory diseases, and skin conditions such as psoriasis are also associated with EGFR overexpression and activation. Accordingly, a preferred aspect of the instant invention provides methods and compositions for the inhibition of EGFR, wherein said inhibition serves as a treatment for EGFR-associated diseases such as cancer and arthritis. In a particularly preferred embodiment, the invention provides methods and compositions for the inhibition of EGFR in which said methods and compositions prevent the formation of an asymmetric dimer interface.

Other pathogenic conditions which have been associated with tyrosine kinases such as EGFR include, without limitation, psoriasis, hepatic cirrhosis, diabetes, angiogenesis, restenosis, ocular diseases, rheumatoid arthritis and other inflammatory disorders, immunological disorders such as autoimmune disease, cardiovascular disease such as atherosclerosis and a variety of renal disorders. Thus, in a preferred aspect of the invention, compositions and methods are provided for the treatment of these EGFR-associated diseases, in which one exemplary embodiment of the invention treats, prevents, ameliorates, or cures the disease by preventing uncontrolled cell differentiation and proliferation.

In another aspect of the invention, compositions and methods are provided for the treatment, amelioration, and prevention of angiogenesis-dependent diseases. In these diseases, vascular growth is excessive or allows unwanted growth of other tissues by providing blood supply. These diseases include angiofibroma, arteriovenous malformations, arthritis, atherosclerotic plaques, corneal graft neovascularization, delayed wound healing, diabetic retinopathy, granulations due to burns, hemangiomas, hemophilic joints, hypertrophic scars, neovascular glaucoma, nonunion fractures, Osler-weber syndrome, psoriasis, pyogenic granuloma, retrolental fibroplasia, scleroderma, solid tumors, trachoma, and vascular adhesions.

By inhibiting vessel formation (angiogenesis), unwanted growth may be slowed or halted, thus ameliorating the disease. In a normal vessel, a single layer of endothelial cells lines the lumen. Growth of a vessel requires proliferation of endothelial cells and smooth muscle cells, which is often dependent on EGFR activation. As such, the present invention provides compositions and methods for the inhibition of EGFR activation.

Pharmaceutical Compositions and Formulations

The invention also encompasses the use of pharmaceutical compositions of the invention or salts thereof to practice the methods of the invention. Such a pharmaceutical composition may consist of at least one compound or conjugate of the invention or a salt thereof in a form suitable for administration to a subject, or the pharmaceutical composition may comprise at least one compound or conjugate of the invention or a salt thereof, and one or more pharmaceutically acceptable carriers, one or more additional ingredients, or some combination of these. The compound or conjugate of the invention may be present in the pharmaceutical composition in the form of a physiologically acceptable salt, such as in combination with a physiologically acceptable cation or anion, as is well known in the art.

In an embodiment, the pharmaceutical compositions useful for practicing the methods of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for oral, rectal, vaginal, parenteral, topical, pulmonary, intranasal, buccal, ophthalmic, or another route of administration. A composition useful within the methods of the invention may be directly administered to the skin, vagina or any other tissue of a mammal. Other contemplated formulations include liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human subject being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist may design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions of the invention are formulated using one or more pharmaceutically acceptable excipients or carriers. In one embodiment, the pharmaceutical compositions of the invention comprise a therapeutically effective amount of a compound or conjugate of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

Formulations may be employed in admixtures with conventional excipients, i.e., pharmaceutically acceptable organic or inorganic carrier substances suitable for oral, vaginal, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an anti-oxidant and a chelating agent that inhibits the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Administration/Dosing

The regimen of administration may affect what constitutes an effective amount a modulator of the invention. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

The compound may be administered to a subject as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, and the type and age of the animal.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

Compounds of the invention for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating the same or another disease as that treated by the compositions of the invention) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound or conjugate of the invention, alone or in combination with a second pharmaceutical agent; and instructions for using the compound or conjugate to treat, prevent, or reduce one or more symptoms of a disease in a subject.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject, or delivering an imaging or diagnostic agent to a subject.

Controlled Release Formulations and Drug Delivery Systems

Controlled- or sustained-release formulations of a pharmaceutical composition of the invention may be made using conventional technology, using for example proteins equipped with pH sensitive domains or protease-cleavable fragments. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gel-caps, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased subject compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In a preferred embodiment of the invention, the compounds of the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

Kits

The present invention includes a kit comprising a modulator compound or composition of the present invention, and an instructional material which describes, for instance, administering the compound or composition to a subject as a therapeutic treatment as described elsewhere herein.

In one embodiment, this kit further comprises a (preferably sterile) pharmaceutically acceptable carrier suitable for dissolving or suspending the therapeutic composition, for instance, prior to administering to a subject. Optionally, the kit comprises an applicator for administering the compound or composition.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1

Cell Permeable, Allosteric Inhibitors of the EGFR and Mutants Thereof

Experiments were designed to determine whether the juxtamembrane segment is an allosteric regulator of kinase activity.

Introduction of the reported helix disrupting R656,657G mutation in EGFR impaired EGF-dependent activation of wild-type EGFR suggesting that disruption of the coiled coil abolishes asymmetric interface. When an EGFR point mutant (V924R) that prevents formation of the asymmetric dimer was expressed in CHO cells, there was no detectable phosphorylation suggesting that disruption of the asymmetric interface may abolish the coiled coil (FIG. 1).

Figure 4:
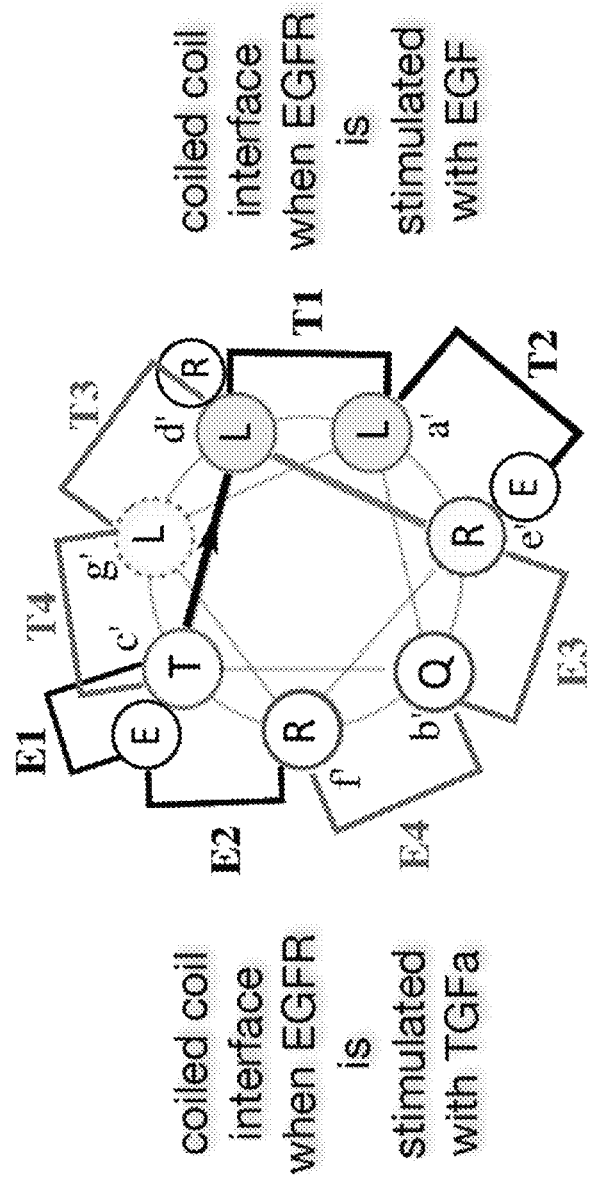
FIG. 4 is a schematic demonstrating that molecules can target different faces of a dimerized juxtamembrane segment.

The next set of experiments was designed to assess the two potential mechanisms of regulating EGFR activity. Peptide mimetics were generated to target the juxtamembrane segment in order to inhibit kinase activity in living cells. One set of peptide mimetics was designed to function by inhibiting coiled coil formation. Another set of peptide mimetics was designed to function by fixing the coiled coil structure (FIG. 2). FIG. 3 lists a representative list of peptide mimetics used in the experiments. FIG. 4 is a schematic showing where the different peptide mimetics target on the face of a dimeric juxtamembrane segment. FIG. 8-FIG. 16 depict the structures of the various peptides used in the experiments.

Figure 6:
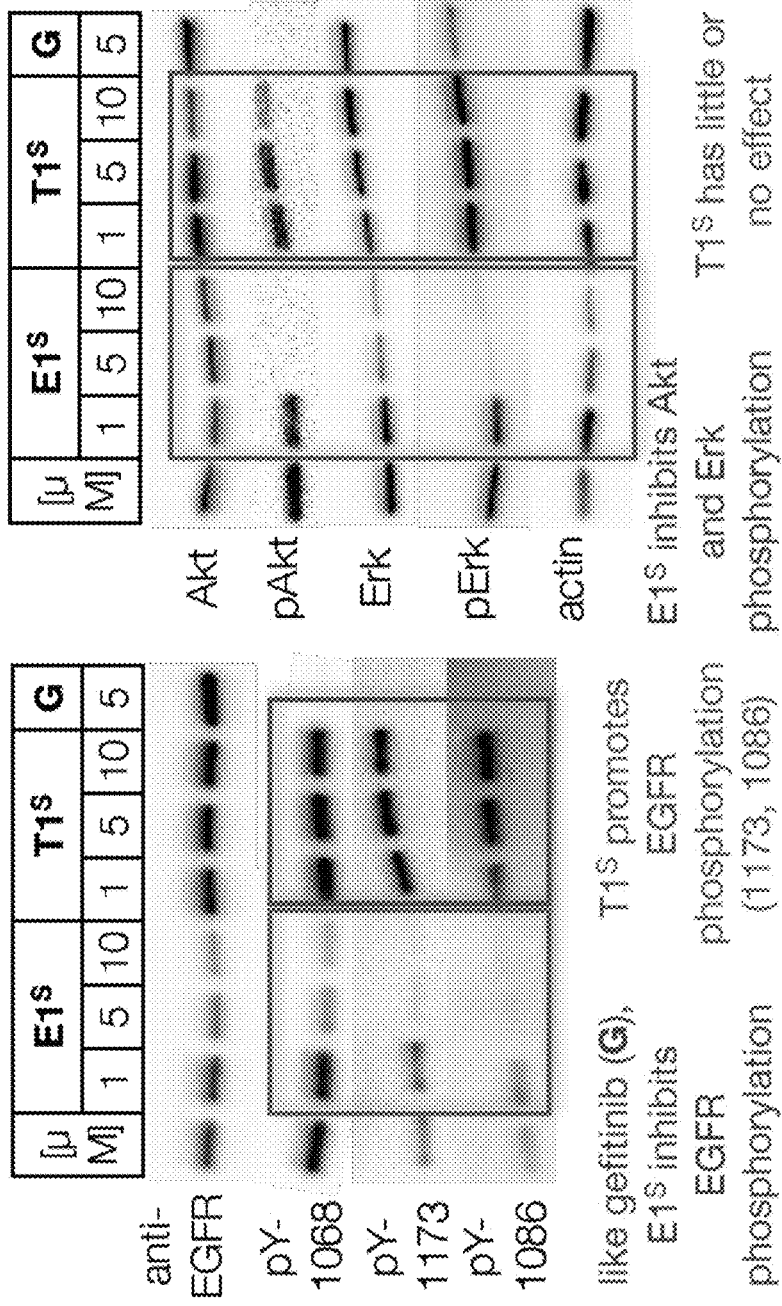
FIG. 6 is an image demonstrating that different families of peptide mimetics affect EGFR signaling in H2030 cells.
Figure 12:
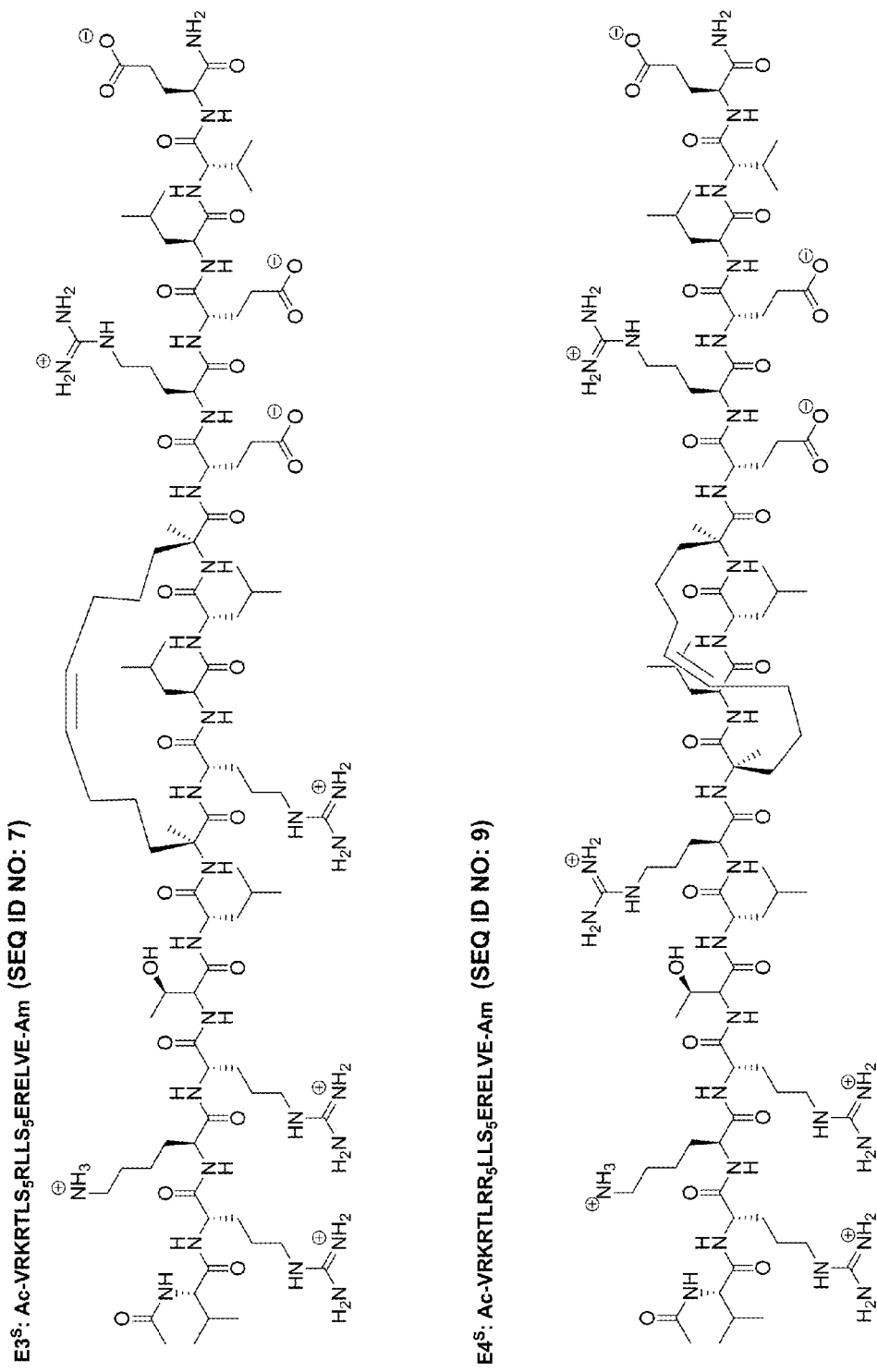
FIG. 12 depicts the structure of $E3^S$ (top) and $E4^S$ (bottom).
Figure 15:
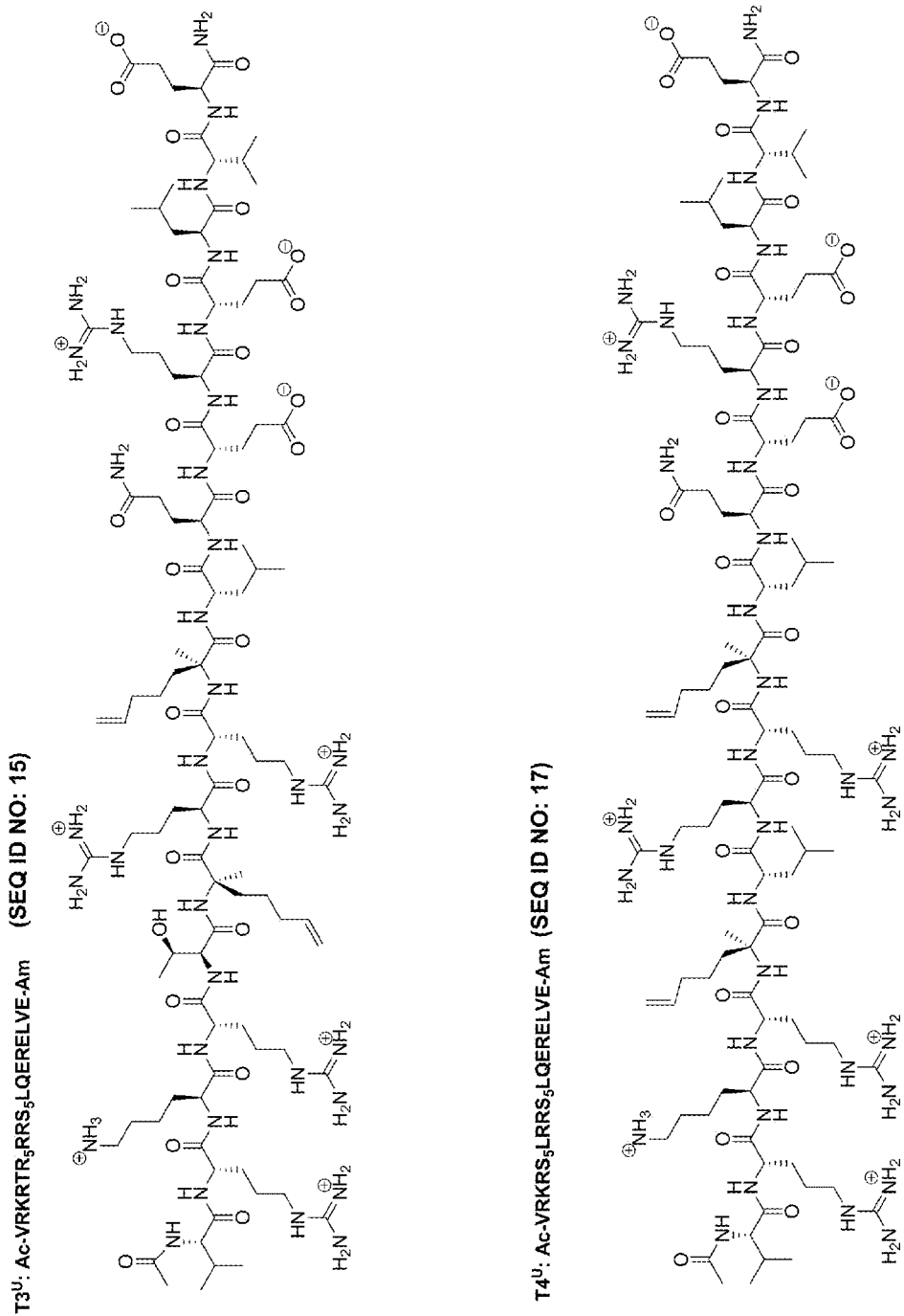
FIG. 15 depicts the structure of $T3^U$ (top) and $T4^U$ (bottom).

Each of the peptide mimetics were applied to cells that expressed EGFR. It was observed that the peptide mimetics exhibited the ability to kill cells that express EGFR (FIG. 5). The peptide mimetics also affected EGFR signaling in cells (FIG. 6).

The results presented herein demonstrate the successful synthesis of novel peptide mimetics that kill lung cancer cells that express wild type EGFR or L858R EGFR or L858R/T790M EGFR. It was observed that $IC_{50}$ value for most potent molecules was about 900 mM. It was observed that no effect of any molecule on viability of cells that do not express EGFR (e.g., SK-N-MC cells). Activity was observed in molecules capable of interacting with both coiled coils (e.g., the one coil formed upon stimulation with EGF and the other coil formed upon stimulation with TGF-α). In some instances, molecules capable of interacting with only one coiled coil did not affect viability. Without wishing to be bound by any particular theory, it is believed that molecules that do not affect viability may still affect signaling.

Without wishing to be bound by any particular theory, it is believed that the strategy for allosteric inhibition of EGFR is applicable to other ErbB family members and other receptor tyrosine kinases (FIG. 7).

Example 2

Inhibiting Epidermal Growth Factor Receptor at a Distance

The Epidermal Growth Factor Receptor (EGFR) (Taylor et al., 1974, J. Biol. Chem., 249, 2188; Cohen et al., 1980, Biol. Chem., 255, 4834; Kawamoto et al., 1983, J. Proc. Natl. Acad. Sci. USA, 80, 1337) tyrosine kinase is implicated in an exceptional number of human cancers (Yarden et al., 2012, Nat Rev Cancer, 12: 553). The vast majority of known EGFR inhibitors target either the extracellular, growth factor-binding domain or the intracellular, ATP-binding domain. Molecules that inhibit the kinase activity of EGFR in a fundamentally new way are described herein. These molecules inhibit EGFR kinase activity by competing with formation of an essential coiled coil located within the (distal) juxtamembrane segment of the assembled protein dimer. The most potent molecules described herein decrease the viability of wild type and mutant EGFR-dependent cells lines and inhibit phosphorylation of both EGFR and downstream targets. Potency is directly correlated with the ability to block coiled coil formation within full length EGFR in cells.

The results of the experiments are now described.

Figure 17A:
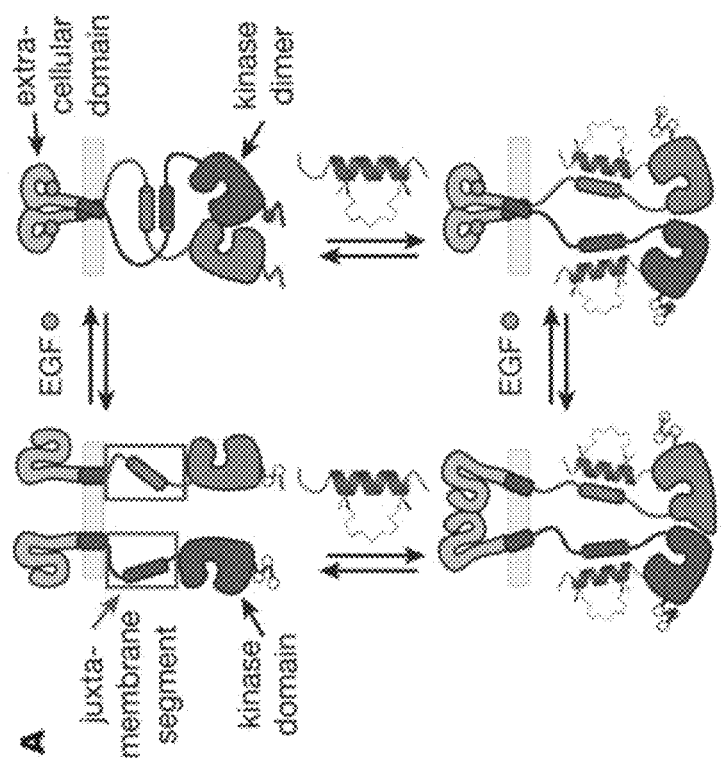
FIG. 17A and FIG. 17B, depicts a set of schematics illustrating the structure and function of exemplary peptides.

Described herein are molecules that inhibit EGFR via allostery, by inhibiting formation of an intra-dimer coiled coil within the juxtamembrane (JM) segment that is essential for assembly of the active, asymmetric kinase dimer (Lewis, et al., 2008, Curr. Opin. Chem. Biol., 12, 269; Schwartz, et al., 2007, Trends Pharmacol. Sci., 28, 366). It was recently reported, using a tool known as bipartite tetracysteine display (Luedtke, et al., 2007, Nat. Chem. Biol., 3, 779; Scheck, et al., 2011, Acc. Chem. Res., 44, 654), that the binding of the epidermal growth factor (EGF) (Carpenter, et al., 1979, Annu. Rev. Biochem., 48, 193) to the extracellular domain of full length EGFR (Taylor et al., 1974, J. Biol. Chem., 249, 2188; Cohen et al., 1980, Biol. Chem., 255, 4834; Kawamoto et al., 1983, J. Proc. Natl. Acad. Sci. USA, 80, 1337) assembles an intra-dimer, antiparallel, coiled coil within the JM segment located between the transmembrane helix and the kinase domain (FIG. 17A) (Scheck, et al., 2012, ACS Chem. Biol., 7, 1367; Jura, et al., 2009, J. Cell, 137, 1293; Endres, et al., 2013, Cell, 152, 543). EGFR variants that lack a JM segment (Thiel, et al., 2007, Proc. Natl. Acad. Sci., 104, 19238) or that contain amino acid substitutions that reduce α-helix propensity (Jura, et al., 2009, J. Cell, 137, 1293; He, et al., 2012, Sci. Rep., 2) are catalytically inactive. Other variants that disfavor assembly of the active, asymmetric kinase dimer (Jura, et al., 2009, J. Cell, 137, 1293) do not support formation of the JM coiled coil (Scheck, et al., 2012, ACS Chem. Biol., 7, 1367). Taken together, these observations suggest that ligands capable of inhibiting coiled coil formation should inhibit the tyrosine kinase activity of EGFR via an allosteric mechanism. Indeed, a simple polypeptide containing the EGFR juxtamembrane segment fused to HIV Tat (TE-64562) inhibits EGFR signaling, but neither its binding mode nor mechanism of action is understood as kinase activity itself was unaffected (Boran, et al., 2012, PLoS ONE, 7, e49702).

Figure 17B:
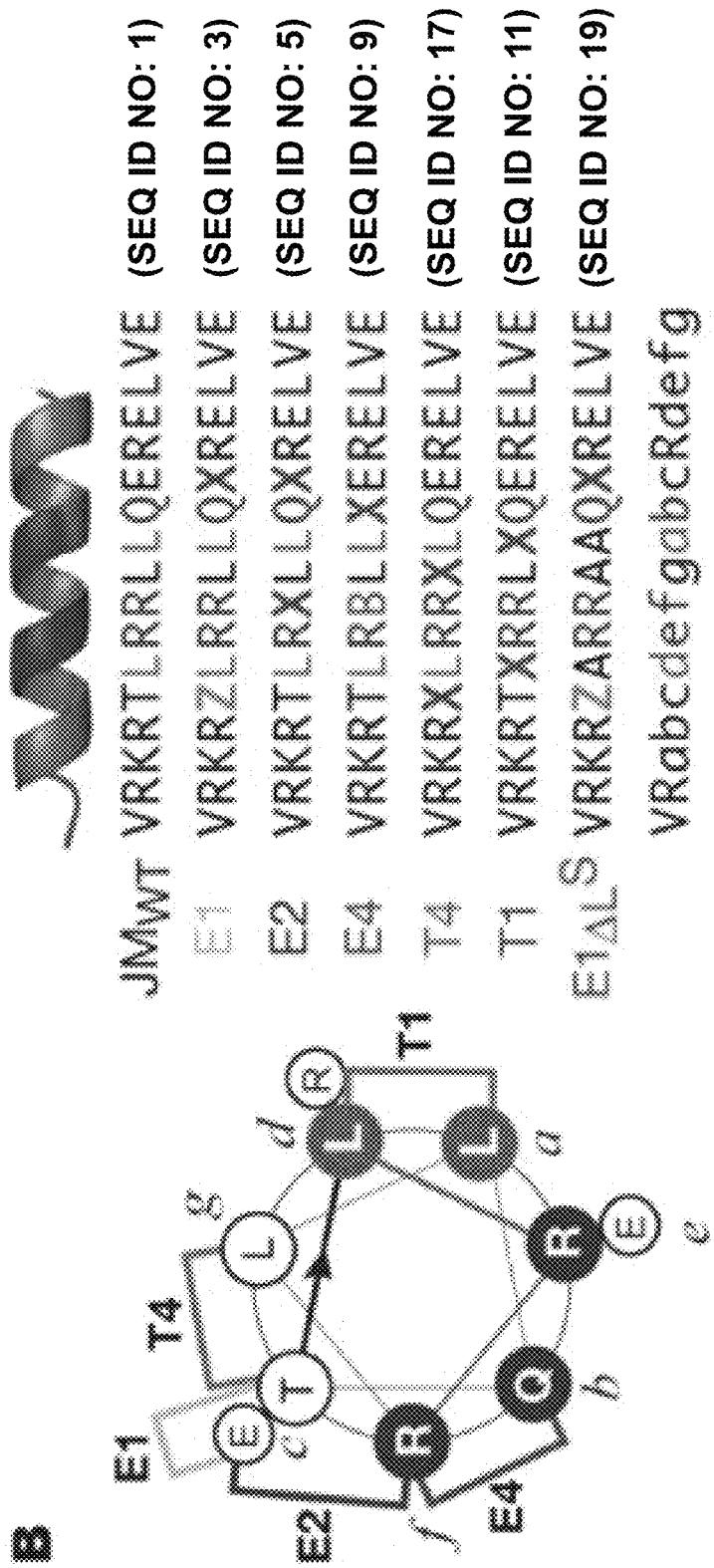

Previous work has shown that peptides containing judiciously positioned i+3, i+4, and i+7 macrocyclic bridges (often referred to as hydrocarbon staples) can display improved α-helix content, protease resistance, and in some cases, cellular uptake, when compared to unmodified peptides with similar sequences (Verdine, et al., 2012, Drug Disc. Today: Technol., 9, e41; Schafineister, et al., 2000, J. Am. Chem. Soc., 122, 5891; Walensky, et al., 2014, J. Med. Chem.). These features make hydrocarbon-stapled peptides uniquely suited to evaluate the JM coiled coil as an allosteric regulatory site for EGFR. To begin this evaluation, five peptides were synthesized, wherein the peptides comprised the 17-residue JM-A segment (EGFR residues 645-662) containing a single hydrocarbon staple at five positions around the helix circumference (FIG. 17B). Four of the variants chosen (E1$^S$, E2$^S$, E4$^S$, and T4$^S$) contain a hydrocarbon staple on the helix face opposite that used for EGF-stimulated coiled coil formation (Scheck, et al., 2012, ACS Chem. Biol., 7, 1367). One (T1S), prepared as a control, contains a hydrocarbon staple that blocks the face used for EGF-stimulated coil formation (Scheck, et al., 2012, ACS Chem. Biol., 7, 1367; Jura, et al., 2009, J. Cell, 137, 1293). Two additional peptides contain the unmodified JM-A sequence fused to HIV Tat (TE-64562) (Boran et al., 2012, PLoS ONE, 7: e49702) or not (JM-WT). All hydrocarbon-stapled peptides displayed greater α-helical content than JM-WT or TE-64562. It was reasoned that if the JM coiled coil regulates EGFR activity via allostery, then ligands E1$^S$, E2$^S$, E4$^S$, and T4$^S$ should inhibit EGFR activity and decrease the viability of EGFR-dependent cell lines, albeit to varying degree, whereas T1$^S$ and JM-WT should have little or no effect.

Figure 18:
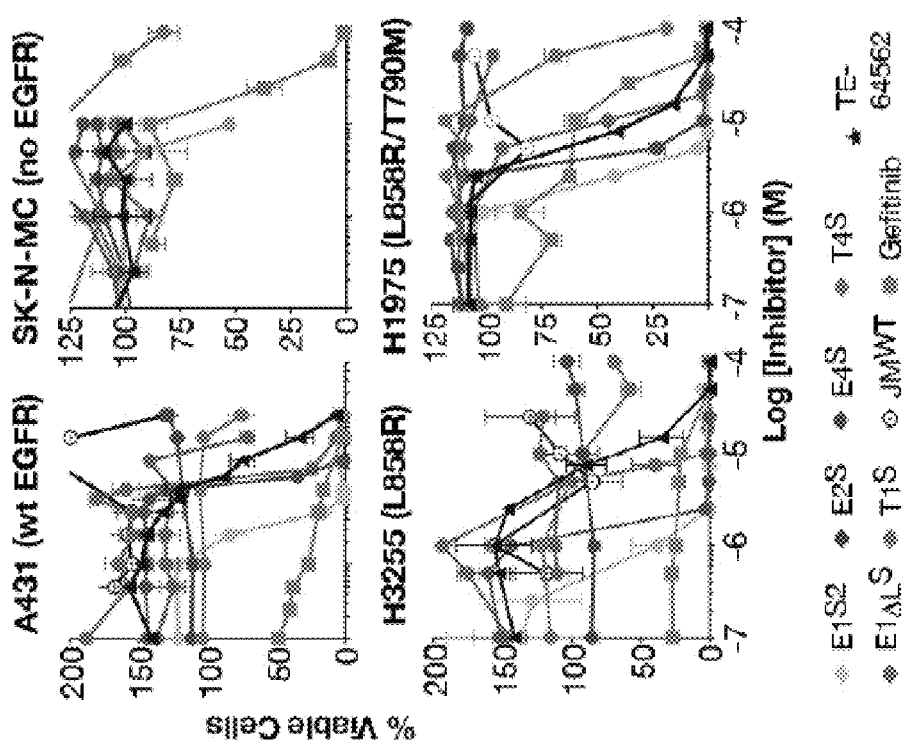
FIG. 18 is a set of graphs depicting the results of example experiments demonstrating the effect of native and hydrocarbon-stapled peptides on cell viability. Plot of % viable cells remaining after 18 h treatment with [ligand] shown. Viability was assessed by monitoring oxyluciferin production by Ultra-Glow™ luciferase, a reaction that requires ATP. Error bars show standard error of the mean.

The effect of each molecule was evaluated on the viability of four EGFR-dependent cell lines that differ in cancer/tissue type as well as ErbB expression level and mutational state and one cell line that does not express EGFR (FIG. 18). A431 and H2030 cells express wild type EGFR, whereas H3255 and H1975 cells express single (L858R) or double (L858R/T790M) mutant forms, respectively; SK-NMC cells express ErbB2 and 4 but not EGFR and ErbB3 (Kawamoto et al., 1983, J. Proc. Natl. Acad. Sci. USA, 80, 1337; Fallon, et al., 2004, J. Neuro-Oncol., 66, 273; Pao, et al., 2005, PLoS Med, 2, 0225; Aifa, et al., 2005, Exp. Cell. Res., 302, 108).

Examination of the dose response curves in FIG. 18 reveals several trends. First, as expected, cells expressing wt EGFR (A431) or the L858R mutant (H3255) are sensitive to gefitinib in the expected concentration range, whereas those expressing the EGFR double mutant (H1975) or no EGFR (SK-N-MC) are not (Eck et al., 2010, Biochim Biophys Acta, Proteins Proteomics, 19: 3159). Second, none of the cells are sensitive to JM-WT, an unmodified (and non-cell permeable) polypeptide containing the EGFR JM-A sequence; fusion of JM-WT to the Tat transactivation domain results in moderate decreases in viability after 18 hours incubation, as reported (Boran, et al., 2012, PLoS ONE, 7, e49702); potency is mitigated significantly after 72 h, perhaps because of degradation.

Most importantly, all EGFR-expressing cell lines are sensitive to one or more hydrocarbon-stapled peptide, with potency following the order $E1^S > E2^S >> T4^S \cong E4^S$. $T1^S$ was inactive in all cell lines tested. In all cases, the most potent inhibitor ($E1^S$) carries the hydrocarbon bridge on the helix face that lies opposite that used for EGF-induced coiled coil formation (Scheck, et al., 2011, Acc. Chem. Res., 44, 654), whereas the least potent molecule ($T1^S$) is bridged within this face, with the bridge replacing two leucine side chains that participate in intra-dimer coiled coil formation (Jura, et al., 2009, J. Cell, 137, 1293). $E1^S$ is ten-fold more potent than $E1_{AL}^S$, in which the two leucines are replaced by alanine, and was between 2 and 10 times more potent than the previously reported TE-64562 polypeptide (Boran, et al., 2012, PLoS ONE, 7, e49702), with the largest difference in H3255 cells that express L858R EGFR. These observations suggest that the decrease in cell viability observed in the presence of $E1^S$ results from a direct interaction of the helical peptide mimetic with the EGFR JM-A region. It is worth noting that $E1^S$, $E2^S$, $T4^S$ and $E4^S$ all carry the hydrocarbon bridge on the helix face opposite the leucines that lie at the inter-dimer coiled coil interface (a and d positions of the helical wheel), yet only $E1^S$ functions as a potent inhibitor.

Figure 19:
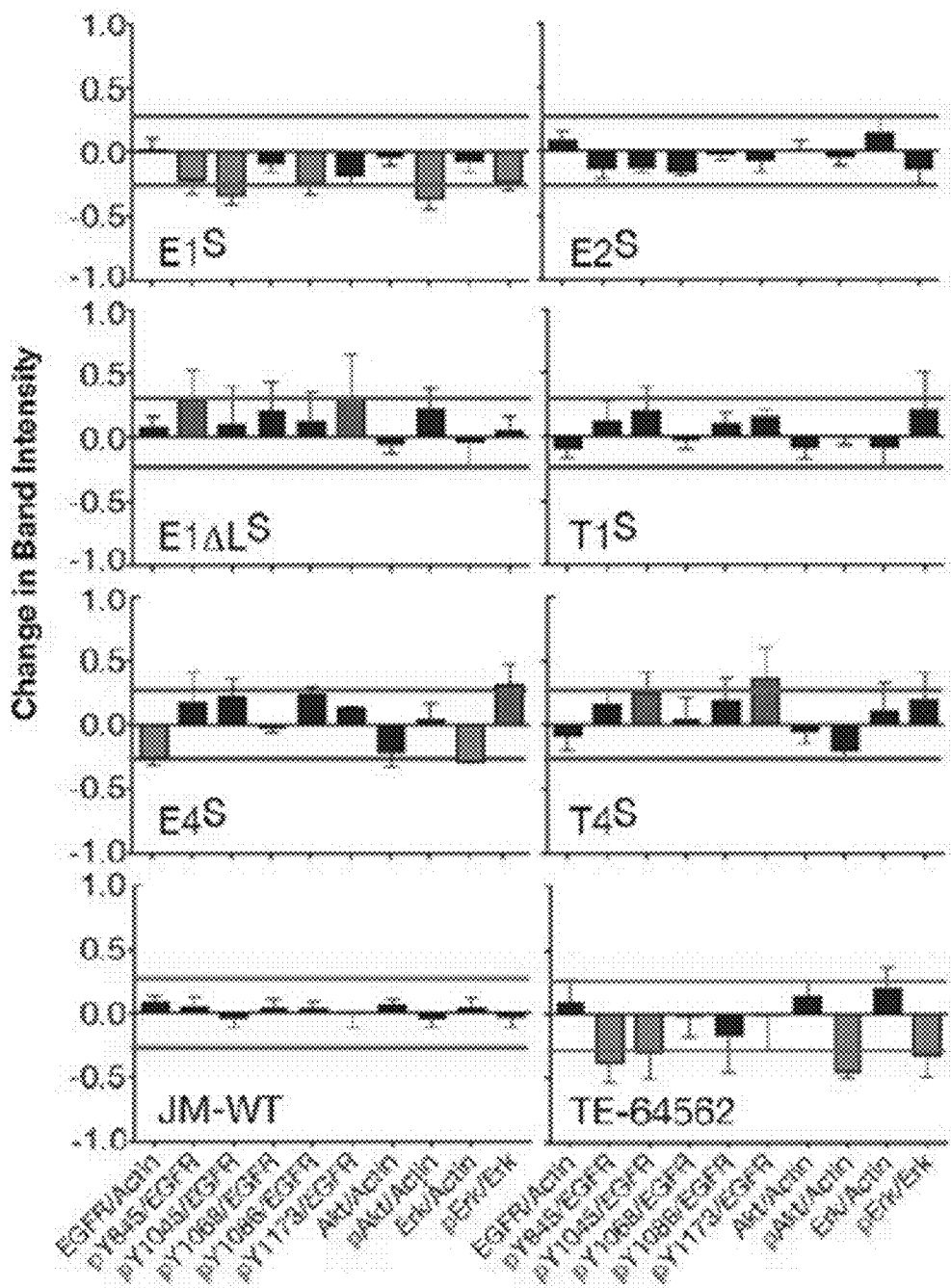
FIG. 19 is a set of graphs depicting the results of example experiments demonstrating the effect of native (JM-WT, TE-64562) and hydrocarbon-stapled peptides on phosphorylation of EGFR, Akt and Erk1/2. A431 cells were treated with 10 μM of the ligand shown for 2 hours, stimulated with 10 ng/mL EGF, then lysed, immunoblotted, and visualized. Plots illustrate the increase or decrease in the intensity of the indicated phospho-protein band between treated and untreated cells. Error bars representing standard error of the mean over at least 4 trials.

Activation of EGFR upon growth factor binding leads to a well characterized pattern of Tyr and Ser/Thr phosphorylation events that initiate downstream signaling networks (Olayioye, et al., 2000, EMBO J., 19, 3159). Molecules that block growth factor binding to the extracellular domain, or ATP binding to the intracellular kinase domain, inhibit the phosphorylation of both EGFR and downstream factors such as Erk and Akt (Yarden, et al., 2012, Nat. Rev. Cancer, 12, 553). Immunoblots were used to evaluate whether the effects of JM-A-derived ligands on the viability of EGFR-dependent cell lines correlated with their effects on EGFR phosphorylation and the activation of downstream factors. Specifically, phosphorylation was probed at EGFR tyrosines 845, 1045, 1068, 1086, and 1173, as well as for phospho-Akt (Ser473) and phospho-Erk1/2 (T202/Y204) (FIG. 19).

Incubation of A431 cells with 10 μM $E1^S$ decreased the level of EGFR phosphorylation at positions Y845, Y1045, and Y1086 (red bars); phosphorylation at Y1068 and Y1173 were affected minimally if at all. A431 cells treated with $E1^S$ also showed decreased levels of phospho-Akt and phospho-Erk; the levels of EGFR, Akt and Erk themselves were unaffected. The pattern of phosphorylation changes induced by $E1^S$ paralleled those observed with TE-64562. $E2^S$ and $E1_{AL}^S$, which had more modest effects on cell viability (FIG. 18), caused little or no decrease in phosphorylation at any position, whereas $T1^S$, $E4^S$, and $T4^S$ led to small increases in phosphorylation at many positions. Thus, in A431 cells, there is a correlation between the effect of JM-A-derived ligands on cell viability and decreases in EGFR autophosphorylation and signaling along the PI3K/Akt and Erk/MAP kinase pathways.

Figure 20:
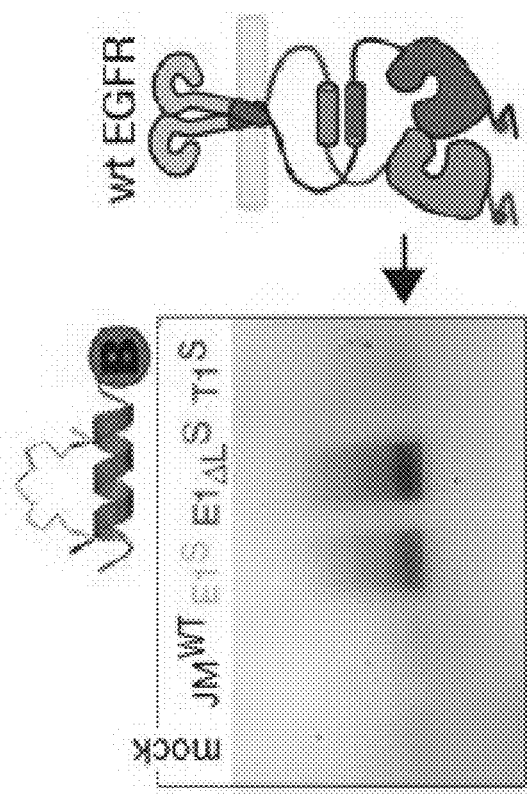
FIG. 20 depicts the results of example experiments demonstrating that $^BE1^S$ and $^BE1_{AL}{}^S$ sequester wtEGFR from CHO-K1 cell lysates. CHO-K1 lysates were treated with 25 μM of each biotinylated peptide shown for 1 hour, then incubated with streptavidin-coated beads overnight. Sequestered proteins were eluted, electrophoresed, and immunoblotted to detect EGFR. Band intensities were measured using ImageJ (Schneider et al., 2012, Nat. Meth., 9: 671).
Figure 21:
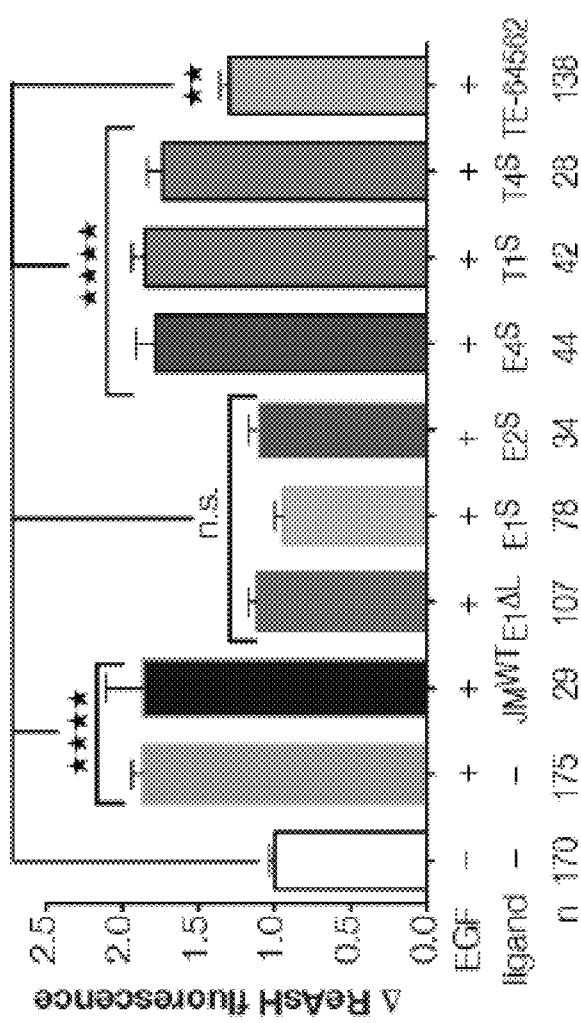
FIG. 21 is a graph depicting the results of example experiments conducted to monitor EGFR intra-dimer coiled coil formation using TIRF and bipartite tetracysteine display. CHO cells were transiently transfected with EGFR CCH-1, treated with 1 μM of the indicated ligand for 1 hour, stimulated with 100 ng/mL EGF for 30 minutes, and labeled with ReAsH (Scheck et al., 2012, ACS Chem Biol, 7: 1367). Plot shows the change in ReAsH fluorescence of n cells after correction for differences in CCH-1 expression. Error bars represent standard error of the mean. *p<0.05, p<0.01, *p<0.001, ****p<0.0001, one-way ANOVA with Bonferroni post-analysis accounting for multiple comparisons.

Two additional experiments were performed to evaluate whether the $E1^S$-induced viability changes and decreases in EGFR and Erk/Akt phosphorylation resulted from a direct interaction with the EGFR JM segment. First, experiments were conducted to evaluate the extent to which biotinylated analogs of $E1^S$ and $T1^S$ as well as JM-WT and $E1_{AL}^S$ ($^B E1^S$, $^B T1^S$, $^B$JM-WT, and $^B E1_{AL}^S$, respectively) could sequester native, full length, EGFR (wtEGFR) from transiently transfected CHO-K1 cell lysates. Each biotinylated analog (25 μM) was incubated for 1 hour with lysates from wtEGFR-expressing cells, and then incubated with Mag-Sepharose Streptavidin Beads overnight. A mock reaction lacking a biotinylated analog was run alongside. After washing, the sequestered proteins were eluted, resolved by SDS-PAGE (10%), probed with a commercial anti-EGFR antibody, visualized using a horseradish peroxidase-tagged mouse anti-rabbit secondary antibody, and quantified with chemiluminescent detection. Both $^B E1^S$ and $^B E1_{AL}^S$ sequestered full length, wild type EGFR from the cell lysates, whereas $^B T1^S$ and $^B$JM-WT did not (FIG. 20). Little or no EGFR was sequestered when no biotinylated peptide was added (mock), providing additional support for a direct interaction between the hydrocarbon-stapled peptide $E1^S$ and the juxtamembrane segment of wild type EGFR.

Finally, a previously reported bipartite tetracysteine display (Luedtke, et al., 2007, Nat. Chem. Biol., 3, 779; Scheck, et al., 2011, Acc. Chem. Res., 44, 654) assay was used to directly probe whether treatment with $E1^S$ inhibited intradimer coiled coil formation within the juxtamembrane segment of full length, activated, EGFR expressed on the mammalian cell surface (Scheck, et al., 2012, ACS Chem. Biol., 7, 1367). Experiments were conducted using CHO cells expressing an EGFR variant (CCH-1) with a cysteine pair within the JM-A whose location supports ReAsH binding and fluorescence upon EGF-induced coiled coil assembly 24. It was reasoned that if $E1^S$ inhibits formation of the JM coiled coil, it should also decrease the ability of CCH-1 to bind ReAsH and fluoresce in the presence of the activating growth factor EGF. CHO cells transiently expressing the EGFR variant CCH-1 on the cell surface were exposed to native and hydrocarbon-stapled peptides, stimulated with EGF, incubated with ReAsH, and the fluorescence increase due to ReAsH quantified using total internal reflectance fluorescence microscopy (TIR-FM). Treatment with EGF alone led to the expected increase in ReAsH fluorescence at the cell surface; this increase was unchanged by the presence of JM-WT, E4S, $T1^S$, or $T4^S$, consistent with both the their inability to decrease the viability of EGFR-expressing cells (FIG. 18) and sequester transfected EGFR from CHO cell lysates (FIG. 19). However, treatment of cells with 1 μM $E1^S$, $E2^S$, $E1_{AL}^S$, and, to a lesser extent, TE-64562, led to a significant loss in ReAsH fluorescence, which is inferred to represent a loss in the coiled coil interaction. At a lower concentration only $E1^S$ and $E1_{AL}^S$ effectively reduced the ReAsH signal. Identical results were observed when cells were treated first with EGF and then with the indicated peptides. None of the peptides tested had any effect on the extent of ReAsH fluorescence in the absence of EGF. This data supports a model in which $E1^S$, $E1_{AL}^S$, $E2^S$, and, to a lesser extent, TE-64562, interact with the EGFR JM segment to inhibit intra-dimer coiled coil formation. Taken with the cell viability and immunoblotting experiments, it is demonstrated herein that $E1^S$ allosterically inhibits EGFR by disrupting the intradimer coiled coil. This work validates the juxtamembrane segment as a viable allosteric target for inhibitor design.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated peptide that inhibits an activity of an epidermal growth factor receptor family protein, wherein the isolated peptide comprises an amino acid sequence selected from the group consisting of SEQ ID NOs: 3, 5, and 17.

2. The peptide of claim 1, wherein the peptide comprises a hydrocarbon staple formed between the two unnatural amino acids of SEQ ID NOs: 3, 5, or 17.

3. The peptide of claim 1, wherein the peptide does not comprise a hydrocarbon staple formed between the two unnatural amino acids of SEQ ID NOs: 3, 5, or 17.

* * * * *

SEQUENCE LISTING

<160> NUMBER OF SEQ ID NOS: 28

<210> SEQ ID NO 1
<211> LENGTH: 17
<212> TYPE: PRT
<213> ORGANISM: Artificial Sequence
<220> FEATURE:
<223> OTHER INFORMATION: Chemically synthesized

<400> SEQUENCE: 1

Val Arg Lys Arg Thr Leu Arg Arg Leu Leu Gln Glu Arg Glu Leu Val
1               5                   10                  15

Glu

<210> SEQ ID NO 2
<211> LENGTH: 17
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (5)..(5)
<223> OTHER INFORMATION: Xaa = any amino acid used in the formation of
      a staple
<220> FEATURE:
<221> NAME/KEY: MISC_FEATURE
<222> LOCATION: (12)..(12)
<223> OTHER INFORMATION: Xaa = any amino acid used in the formation of
      a staple

<400> SEQUENCE: 2

Val Arg Lys Arg Xaa Leu Arg Arg Leu Leu Gln Xaa Arg Glu Leu Val
1               5                   10                  15

Glu

<210> SEQ ID NO 3
<211> LENGTH: 17
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (5)..(5)
<223> OTHER INFORMATION: Xaa = (R)-2-(7'-octenyl)alanine (also referred
      to as Z or R8)
<220> FEATURE:
<221> NAME/KEY: MISC_FEATURE
<222> LOCATION: (12)..(12)
<223> OTHER INFORMATION: Xaa = (S)-2-(4'-pentenyl)alanine (also referred
      to as X or S5)

<400> SEQUENCE: 3

Val Arg Lys Arg Xaa Leu Arg Arg Leu Leu Gln Xaa Arg Glu Leu Val
1               5                   10                  15

Glu

<210> SEQ ID NO 4
<211> LENGTH: 17
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (8)..(8)
<223> OTHER INFORMATION: Xaa = any amino acid used in the formation of a
      staple

```
<220> FEATURE:
<221> NAME/KEY: MISC_FEATURE
<222> LOCATION: (12)..(12)
<223> OTHER INFORMATION: Xaa = any amino acid used in the formation of a
      staple

<400> SEQUENCE: 4

Val Arg Lys Arg Thr Leu Arg Xaa Leu Leu Gln Xaa Arg Glu Leu Val
1               5                   10                  15

Glu

<210> SEQ ID NO 5
<211> LENGTH: 17
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (8)..(8)
<223> OTHER INFORMATION: Xaa = (S)-2-(4'-pentenyl)alanine (also referred
      to as X or S5)
<220> FEATURE:
<221> NAME/KEY: MISC_FEATURE
<222> LOCATION: (12)..(12)
<223> OTHER INFORMATION: Xaa = (S)-2-(4'-pentenyl)alanine (also referred
      to as X or S5)

<400> SEQUENCE: 5

Val Arg Lys Arg Thr Leu Arg Xaa Leu Leu Gln Xaa Arg Glu Leu Val
1               5                   10                  15

Glu

<210> SEQ ID NO 6
<211> LENGTH: 17
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (7)..(7)
<223> OTHER INFORMATION: Xaa = any amino acid used in the formation of a
      staple
<220> FEATURE:
<221> NAME/KEY: MISC_FEATURE
<222> LOCATION: (11)..(11)
<223> OTHER INFORMATION: Xaa = any amino acid used in the formation of a
      staple

<400> SEQUENCE: 6

Val Arg Lys Arg Thr Leu Xaa Arg Leu Leu Xaa Glu Arg Glu Leu Val
1               5                   10                  15

Glu

<210> SEQ ID NO 7
<211> LENGTH: 17
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (7)..(7)
<223> OTHER INFORMATION: Xaa = (S)-2-(4'-pentenyl)alanine (also referred
      to as X or S5)
```

-continued

```
<220> FEATURE:
<221> NAME/KEY: MISC_FEATURE
<222> LOCATION: (11)..(11)
<223> OTHER INFORMATION: Xaa = (S)-2-(4'-pentenyl)alanine (also referred
      to as X or S5)

<400> SEQUENCE: 7

Val Arg Lys Arg Thr Leu Xaa Arg Leu Leu Xaa Glu Arg Glu Leu Val
1               5                   10                  15

Glu

<210> SEQ ID NO 8
<211> LENGTH: 17
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (8)..(8)
<223> OTHER INFORMATION: Xaa = any amino acid used in the formation of a
      staple
<220> FEATURE:
<221> NAME/KEY: MISC_FEATURE
<222> LOCATION: (11)..(11)
<223> OTHER INFORMATION: Xaa = any amino acid used in the formation of a
      staple

<400> SEQUENCE: 8

Val Arg Lys Arg Thr Leu Arg Xaa Leu Leu Xaa Glu Arg Glu Leu Val
1               5                   10                  15

Glu

<210> SEQ ID NO 9
<211> LENGTH: 17
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (8)..(8)
<223> OTHER INFORMATION: Xaa = (R)-2-(4'-pentenyl)alanine (also referred
      to as B or R5)
<220> FEATURE:
<221> NAME/KEY: MISC_FEATURE
<222> LOCATION: (11)..(11)
<223> OTHER INFORMATION: Xaa = (S)-2-(4'-pentenyl)alanine (also referred
      to as X or S5)

<400> SEQUENCE: 9

Val Arg Lys Arg Thr Leu Arg Xaa Leu Leu Xaa Glu Arg Glu Leu Val
1               5                   10                  15

Glu

<210> SEQ ID NO 10
<211> LENGTH: 17
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (6)..(6)
<223> OTHER INFORMATION: Xaa = any amino acid used in the formation of a
      staple
```

```
<220> FEATURE:
<221> NAME/KEY: MISC_FEATURE
<222> LOCATION: (10)..(10)
<223> OTHER INFORMATION: Xaa = any amino acid used in the formation of a
      staple

<400> SEQUENCE: 10

Val Arg Lys Arg Thr Xaa Arg Arg Leu Xaa Gln Glu Arg Glu Leu Val
1               5                   10                  15

Glu

<210> SEQ ID NO 11
<211> LENGTH: 17
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (6)..(6)
<223> OTHER INFORMATION: Xaa = (S)-2-(4'-pentenyl)alanine (also referred
      to as X or S5)
<220> FEATURE:
<221> NAME/KEY: MISC_FEATURE
<222> LOCATION: (10)..(10)
<223> OTHER INFORMATION: Xaa = (S)-2-(4'-pentenyl)alanine (also referred
      to as X or S5)

<400> SEQUENCE: 11

Val Arg Lys Arg Thr Xaa Arg Arg Leu Xaa Gln Glu Arg Glu Leu Val
1               5                   10                  15

Glu

<210> SEQ ID NO 12
<211> LENGTH: 17
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa = any amino acid used in the formation of a
      staple
<220> FEATURE:
<221> NAME/KEY: MISC_FEATURE
<222> LOCATION: (14)..(14)
<223> OTHER INFORMATION: Xaa = any amino acid used in the formation of a
      staple

<400> SEQUENCE: 12

Val Arg Lys Arg Thr Leu Arg Arg Leu Xaa Gln Glu Arg Xaa Leu Val
1               5                   10                  15

Glu

<210> SEQ ID NO 13
<211> LENGTH: 17
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa = (S)-2-(4'-pentenyl)alanine (also referred
      to as X or S5)
```

```
<220> FEATURE:
<221> NAME/KEY: MISC_FEATURE
<222> LOCATION: (14)..(14)
<223> OTHER INFORMATION: Xaa = (S)-2-(4'-pentenyl)alanine (also referred
      to as X or S5)

<400> SEQUENCE: 13

Val Arg Lys Arg Thr Leu Arg Arg Leu Xaa Gln Glu Arg Xaa Leu Val
1               5                   10                  15

Glu

<210> SEQ ID NO 14
<211> LENGTH: 17
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (6)..(6)
<223> OTHER INFORMATION: Xaa = any amino acid used in the formation of a
      staple
<220> FEATURE:
<221> NAME/KEY: MISC_FEATURE
<222> LOCATION: (9)..(9)
<223> OTHER INFORMATION: Xaa = any amino acid used in the formation of a
      staple

<400> SEQUENCE: 14

Val Arg Lys Arg Thr Xaa Arg Arg Xaa Leu Gln Glu Arg Glu Leu Val
1               5                   10                  15

Glu

<210> SEQ ID NO 15
<211> LENGTH: 17
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (6)..(6)
<223> OTHER INFORMATION: Xaa = (R)-2-(4'-pentenyl)alanine (also referred
      to as B or R5)
<220> FEATURE:
<221> NAME/KEY: MISC_FEATURE
<222> LOCATION: (9)..(9)
<223> OTHER INFORMATION: Xaa = (S)-2-(4'-pentenyl)alanine (also referred
      to as X or S5)

<400> SEQUENCE: 15

Val Arg Lys Arg Thr Xaa Arg Arg Xaa Leu Gln Glu Arg Glu Leu Val
1               5                   10                  15

Glu

<210> SEQ ID NO 16
<211> LENGTH: 17
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (5)..(5)
<223> OTHER INFORMATION: Xaa = any amino acid used in the formation of a
      staple
```

```
<220> FEATURE:
<221> NAME/KEY: MISC_FEATURE
<222> LOCATION: (9)..(9)
<223> OTHER INFORMATION: Xaa = any amino acid used in the formation of a
      staple

<400> SEQUENCE: 16

Val Arg Lys Arg Xaa Leu Arg Arg Xaa Leu Gln Glu Arg Glu Leu Val
1               5                   10                  15

Glu

<210> SEQ ID NO 17
<211> LENGTH: 17
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (5)..(5)
<223> OTHER INFORMATION: Xaa = (S)-2-(4'-pentenyl)alanine (also referred
      to as X or S5)
<220> FEATURE:
<221> NAME/KEY: MISC_FEATURE
<222> LOCATION: (9)..(9)
<223> OTHER INFORMATION: Xaa = (S)-2-(4'-pentenyl)alanine (also referred
      to as X or S5)

<400> SEQUENCE: 17

Val Arg Lys Arg Xaa Leu Arg Arg Xaa Leu Gln Glu Arg Glu Leu Val
1               5                   10                  15

Glu

<210> SEQ ID NO 18
<211> LENGTH: 17
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (5)..(5)
<223> OTHER INFORMATION: Xaa = alpha-aminoisobutyric acid
<220> FEATURE:
<221> NAME/KEY: MISC_FEATURE
<222> LOCATION: (12)..(12)
<223> OTHER INFORMATION: Xaa = alpha-aminoisobutyric acid

<400> SEQUENCE: 18

Val Arg Lys Arg Xaa Leu Arg Arg Leu Leu Gln Xaa Arg Glu Leu Val
1               5                   10                  15

Glu

<210> SEQ ID NO 19
<211> LENGTH: 17
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (5)..(5)
<223> OTHER INFORMATION: Xaa = (R)-2-(7'-octenyl)alanine (also referred
      to as Z or R8)
<220> FEATURE:
<221> NAME/KEY: MISC_FEATURE
<222> LOCATION: (12)..(12)
<223> OTHER INFORMATION: Xaa = (S)-2-(4'-pentenyl)alanine (also referred
      to as X or S5)
```

<400> SEQUENCE: 19

Val Arg Lys Arg Xaa Ala Arg Arg Ala Ala Gln Xaa Arg Glu Leu Val
1               5                   10                  15

Glu

<210> SEQ ID NO 20
<211> LENGTH: 32
<212> TYPE: PRT
<213> ORGANISM: Artificial Sequence
<220> FEATURE:
<223> OTHER INFORMATION: Chemically synthesized

<400> SEQUENCE: 20

Arg Lys Lys Arg Arg Gln Arg Arg Gly Arg Arg His Ile Val
1               5                   10                  15

Arg Lys Arg Thr Leu Arg Leu Leu Gln Glu Arg Glu Leu Val Glu
            20                  25                  30

<210> SEQ ID NO 21
<211> LENGTH: 28
<212> TYPE: PRT
<213> ORGANISM: Artificial Sequence
<220> FEATURE:
<223> OTHER INFORMATION: Chemically synthesized

<400> SEQUENCE: 21

Arg Arg Arg His Ile Val Arg Lys Arg Thr Leu Arg Leu Leu Gln
1               5                   10                  15

Glu Arg Glu Leu Val Glu Pro Leu Thr Pro Ser Gly
            20                  25

<210> SEQ ID NO 22
<211> LENGTH: 28
<212> TYPE: PRT
<213> ORGANISM: Artificial Sequence
<220> FEATURE:
<223> OTHER INFORMATION: Chemically synthesized

<400> SEQUENCE: 22

Arg Arg Gln Gln Lys Ile Arg Lys Tyr Thr Met Arg Arg Leu Leu Gln
1               5                   10                  15

Glu Thr Glu Leu Val Glu Pro Leu Thr Pro Ser Gly
            20                  25

<210> SEQ ID NO 23
<211> LENGTH: 28
<212> TYPE: PRT
<213> ORGANISM: Artificial Sequence
<220> FEATURE:
<223> OTHER INFORMATION: Chemically synthesized

<400> SEQUENCE: 23

Arg Gly Arg Arg Ile Gln Asn Lys Arg Ala Met Arg Arg Tyr Leu Glu
1               5                   10                  15

Arg Gly Glu Ser Ile Glu Pro Leu Asp Pro Ser Glu
            20                  25

<210> SEQ ID NO 24
<211> LENGTH: 27
<212> TYPE: PRT
<213> ORGANISM: Artificial Sequence
<220> FEATURE:
<223> OTHER INFORMATION: Chemically synthesized -continued

```
<400> SEQUENCE: 24

Arg Arg Lys Ser Ile Lys Lys Lys Arg Ala Leu Arg Arg Phe Leu Glu
1               5                   10                  15

Thr Glu Leu Val Glu Pro Leu Thr Pro Ser Gly
            20                  25

<210> SEQ ID NO 25
<211> LENGTH: 9
<212> TYPE: PRT
<213> ORGANISM: Artificial Sequence
<220> FEATURE:
<223> OTHER INFORMATION: Chemically synthesized

<400> SEQUENCE: 25

Phe Arg Ala Ile Met Arg Asp Ile Asn
1               5

<210> SEQ ID NO 26
<211> LENGTH: 9
<212> TYPE: PRT
<213> ORGANISM: Artificial Sequence
<220> FEATURE:
<223> OTHER INFORMATION: Chemically synthesized

<400> SEQUENCE: 26

Phe Arg Ala Ile Ile Arg Asp Leu Asn
1               5

<210> SEQ ID NO 27
<211> LENGTH: 9
<212> TYPE: PRT
<213> ORGANISM: Artificial Sequence
<220> FEATURE:
<223> OTHER INFORMATION: Chemically synthesized

<400> SEQUENCE: 27

Phe Arg Ala Val Ile Arg Asp Leu Asn
1               5

<210> SEQ ID NO 28
<211> LENGTH: 21
<212> TYPE: PRT
<213> ORGANISM: Artificial Sequence
<220> FEATURE:
<223> OTHER INFORMATION: Chemically synthesized

<400> SEQUENCE: 28

Arg Arg Arg His Ile Val Arg Lys Arg Thr Leu Arg Leu Leu Gln Glu
1               5                   10                  15

Arg Glu Leu Val Glu
            20
```